US00RE43166E

(19) United States
(12) Reissued Patent
Sato et al.

(10) Patent Number: US RE43,166 E
(45) Date of Reissued Patent: Feb. 7, 2012

(54) GENE ENCODING CHONDROITINASE ABC AND USES THEREFOR

(75) Inventors: Nobuyuki Sato, Ibaraki (JP); Masahiko Shimada, Ibaraki (JP); Hiroshi Oda, Ibaraki (JP)

(73) Assignee: Maruha Nichiro Foods, Inc., Tokyo (JP)

(21) Appl. No.: 12/613,119

(22) Filed: Nov. 5, 2009

Related U.S. Patent Documents

Reissue of:
(64) Patent No.: 7,008,783
Issued: Mar. 7, 2006
Appl. No.: 08/488,960
Filed: Jun. 7, 1995

U.S. Applications:
(60) Continuation of application No. 08/184,435, filed on Jan. 14, 1994, now abandoned, which is a division of application No. 08/074,349, filed on Jun. 8, 1993, now abandoned.

(30) Foreign Application Priority Data

Sep. 22, 1992 (JP) ..... 4-253016
Feb. 24, 1993 (JP) ..... 5-35810

(51) Int. Cl.

| | |
|---|---|
| ***C12N 15/60*** | (2006.01) |
| ***C12N 15/63*** | (2006.01) |
| ***C12N 5/10*** | (2006.01) |
| ***C12N 1/00*** | (2006.01) |
| ***C12N 1/21*** | (2006.01) |
| *C12N 9/88* | (2006.01) |

(52) U.S. Cl. ..... 435/232; 435/320.1; 435/252.3; 435/252.33; 435/254.11; 435/325; 435/69.1; 536/23.2

(58) Field of Classification Search ..... None
See application file for complete search history.

(56) References Cited

U.S. PATENT DOCUMENTS

| | | | |
|---|---|---|---|
| 4,652,639 | A | 3/1987 | Stabinsky |
| 4,695,816 | A | 9/1987 | Essig et al. |
| 4,696,816 | A | 9/1987 | Brown |
| 5,198,355 | A | 3/1993 | Kikuchi et al. |
| 5,292,509 | A | 3/1994 | Hageman |

FOREIGN PATENT DOCUMENTS

| | | | |
|---|---|---|---|
| EP | 0 355 831 | | 2/1990 |
| EP | 0355831 | B1 | 2/1990 |
| EP | 0-576-294 | | 12/1993 |
| EP | 0576294 | B1 | 12/1993 |
| WO | 91/06303 | A1 | 5/1991 |
| WO | 91/16070 | A1 | 10/1991 |
| WO | WO 91/16070 | | 10/1991 |

OTHER PUBLICATIONS

S.L. Keener et al. "Cloning and Characterization of recA Genes from *Proteus vulagris, Erwinia cartovora, Shigella flexeri,* and *Escherichia coli* B/r", J. Bacteriology 160(1): 153-160. (Oct. 1984).*

T. Maejima et al. "Cloning and Expression of the Gene(s) for Chromosome-Mediated β-Lactamase Production of *Proteus vulgaris* in *Escheichia coli",* Plasmid 18: 120-126. (1987).*

F. Sor et al. "Cloning and DNA Sequence Determination of the L11 Ribosomal Protein Operon of *Serratia marcescens* and *Proteus vulgaris:* Translational Feedback Regulation of the *Escherichia* coil L11 Operon by Heterologous L1 Proteins", Mol. Gen. Genet. 210: 52-59 (1987).*

Berger, Shelby L. et al., "Guide to Molecular Cloning Techniques," Methods in Enzymology, vol. 152, pp. 393-399, 415-423, 432-447 and 661-704 (1987).

Breen, Moira et al., "Microanalysis of Glycosaminoglycans," Analytical Biochemistry, vol. 113:416-422 (1981).

Brittis, Perry A. et al., "Chondroitin Sulfate as a Regulator of Neuronal Patterning in the Retina," Science, vol. 255 (5045):733-736 (1992).

Brown, Mark D., Intradiscal Therapy, Year Book Medical Publishers, Inc., New York (1983) Table of Contents.

Caterson, Bruce et al., "Modulation of native chondroitin sulphate structure in tissue development and in disease," Journal of Cell Science, vol. 97:411-417 (1990).

Deutsher, Murray P., "Guide to Protein Purification," Methods in Enzymology, vol. 182, pgs. 602-613, 738-751 (1990).

Guthrie, Ellen P. et al., "Evidence that the *Bacteroides thetaiotaomicron* Chondroitin Lyase II Gene Is Adjacent to the Chondro-4-Sulfatase Gene and May Be Part of the Same Operon," Journal of Bacteriology, vol. 169(3):1192-1199 (1987).

Henderson, Nigel et al., "Nucleolysis of the Rabbit Intervertebral Disc Using Chondroitinase ABC," Spine, vol. 16 (2):203-208 (1991).

Kato, Fumihiko et al., "Experimental Chemonucleolysis with Chondroitinase ABC," Clin. Orthop. Relat. Res., vol. 253:301-308 (1990).

Linker, Alfred et al., "The Formation of Unsturated Disacharides from Mucopolysaccharides and Their Cleavage to a-Keto Acid by Bacterial Enzymes," The Journal of Biological Chemistry, vol. 235(11):3061-3065 (1960).

McKeon, Robert J. et al., "Reduction of Neurite Outgrowth in a Model of Glial Scarring following CNS Injury Is Correlated with the Expression of Inhibitory Molecules on Reactive Astrocytes," The Journal of Neuroscience, vol. 11 (11):3398-3411 (1991).

(Continued)

*Primary Examiner* — Rebecca Prouty
(74) *Attorney, Agent, or Firm* — Nelson Mullins Riley & Scarborough LLP; Jane E. Remillard, Esq.; Jill Gorny Sloper, Esq.

(57) ABSTRACT

Nucleic acid sequences coding for the chondroitinase ABC gene and isolated chondroitinase ABE protein produced in a host cell transformed with a nucleic acid vector directing the expression of a nucleotide sequence coding for chondroitinase ABE protein described. Chondroitinase ABC prepared by chemical synthesis also described. Monoclonal and polyclonal antibodies which are specifically reactive with chondroitinase ABC protein are disclosed. The isolated chondroitinase ABC can be used in methods of treating intervertebral disc replacement, promoting neurite regeneration, and detecting galactosaminoglycans.

17 Claims, 10 Drawing Sheets

OTHER PUBLICATIONS

Pettipher, E.R. et al., "Cartilage Proteoglycan Depletion in Acute and Chronic Antigen-induced Arthritis," Arthritis and Rheumatism, vol. 32(5):601-607 (1989).

Reissig, Jose L. et al., "A Modified Colorimetric Method for the Estimation of N-Acetylamino Sugars," J. Biol. Chem., vol. 217:959-966 (1955).

Saito, Hidehiko et al., "Enzymatic Methods for the Determination of Small Quantities of Isomeric Chondroitin Sulfates," The Journal of Biological Chemistry, vol. 243(7):1536-1542 (1968).

Sato, Nobuyuki et al., "Cultural Conditions for the Induction of Chondroitinase ABC in *Proteus vulgaris* Cells," J. Ferment. Technol., vol. 64(2):155-159 (1986).

Sato, Nobuyuki et al., "Depolymerization of Chondroitin C Sulfate by Immobilized *Proteus vulgaris* Cells," Biotechnology and Bioengineering, vol. XXVIII:1707-1712 (1986).

Sato, Nobuyuki et al., "Growth-Promoting Activity of Tuna Growth Hormone and Expression of Tuna Growth Hormone cDNA in *Escherichia coli,"* Biotechnology and Applied Biochemistry, vol. 10:385-393 (1988).

Sato, Nobuyuki et al., "Subunit Structure of Chondroitinase ABC from *Proteus vulgaris,"* Agric. Biol. Chem., vol. 50 (4):1057-1059 (1986).

Seibel, Markus J. et al., "Antigenic Properties of Keratan Sulfate: Influence of Antigen Structure, Monoclonal Antibodies, and Antibody Valency," Archives of Biochemistry and Biophysics, vol. 296(2):410-418 (1992).

Thurston, C.F., "Induction and Catabolite Repression of Chondroitinase in Batch and Chemostat Cultures of *Proteus vulgaris,"* Journal of General Microbiology, vol. 80:515-522 (1974).

Yamagata, Tatsuya et al., "Purification and Properties of Bacterial Chondroitinases and Chondrosulfatases," The Journal of Biological Chemistry, vol. 243(7):1523-1535 (1968).

European Search Report for Application No. 94250046, dated Jul. 27, 1994.

M. P. Deutscher (ed.) "Guide to Protein Parification" Meth. Enzeymol. 182:602-613, 738-751 (1990).*

S. L. Beger et al. (eds.) "Guide to Molecular Cloning Techniques" Meth. Enzymol. 152: 393-399, 415-423, 432-447, 661-704 (1987).*

M. Yamagata et al. "Purification and Propertion of Bacterial . . . " J. Biol Chem. 243: 1523-1535 (1968).*

Breen, M. et al., "Microanalysis of Glycosaminoglycans" *Analytical Biochemistry,* vol. 113, pp. 416-422, 1981.

Kato, F. et al., "Experimental Chemonucleolysis With Chondroitinase ABC" *Clin. Orthop.,* vol. 253, pp. 301-308, 1990.

Yamagata et al., "Purification and Properties of Bacterial Chondroitinases and Chondrosulfatases" *The Journal of Biological Chemistry,* vol. 243, No. 7, pp. 1523-1535, (Apr. 10, 1968).

* cited by examiner

```
The N-terminal amino acid sequence of ChSase
 1   2   3   4   5   6   7   8   9  10  11  12  13  14  15  16  17  18 (A.A.)
Ala-Thr-Ser-Asn-Pro-Ala-Phe-Asp-Pro-Lys-Asn-Leu-Met-Gln-Ser-Glu-Ile-Tyr

GCU ACU UCU AAU CCU GC                                  UAC GUU AGU CUU UAU AU
  C   C   C   C   C                                           C   C   C
  A   A   A       A     -P-1                                    A       A       -P-3
  G   G   G       G                (Sense)  (Antisense)        G       G
        AGU                                                   UCA
          C             -P-2                                    G               -P-4
```

Fig. 1A

```
 1   2   3   4   5   6   7   8   9  10  11  12  13  14  15  16  17  18
Ala-Thr-Ser-Asn-Pro-Ala-Phe-Asp-Pro-Lys-Asn-Leu-Met-Gln-Ser-Glu-Ile-Tyr

GCA ACC AGC AAT CCT GCA TTT GAT CCT AAA AAT CTG ATG CAG TCC GAA ATT TA
        Primer A                    Probe
CGT TGG TCG TTA GGA CGT AAA CTA GGA TTT TTA GAC TAC GTC AGG CTT TAA AT
                                                    Primer B
```

Fig. 1B

Amended

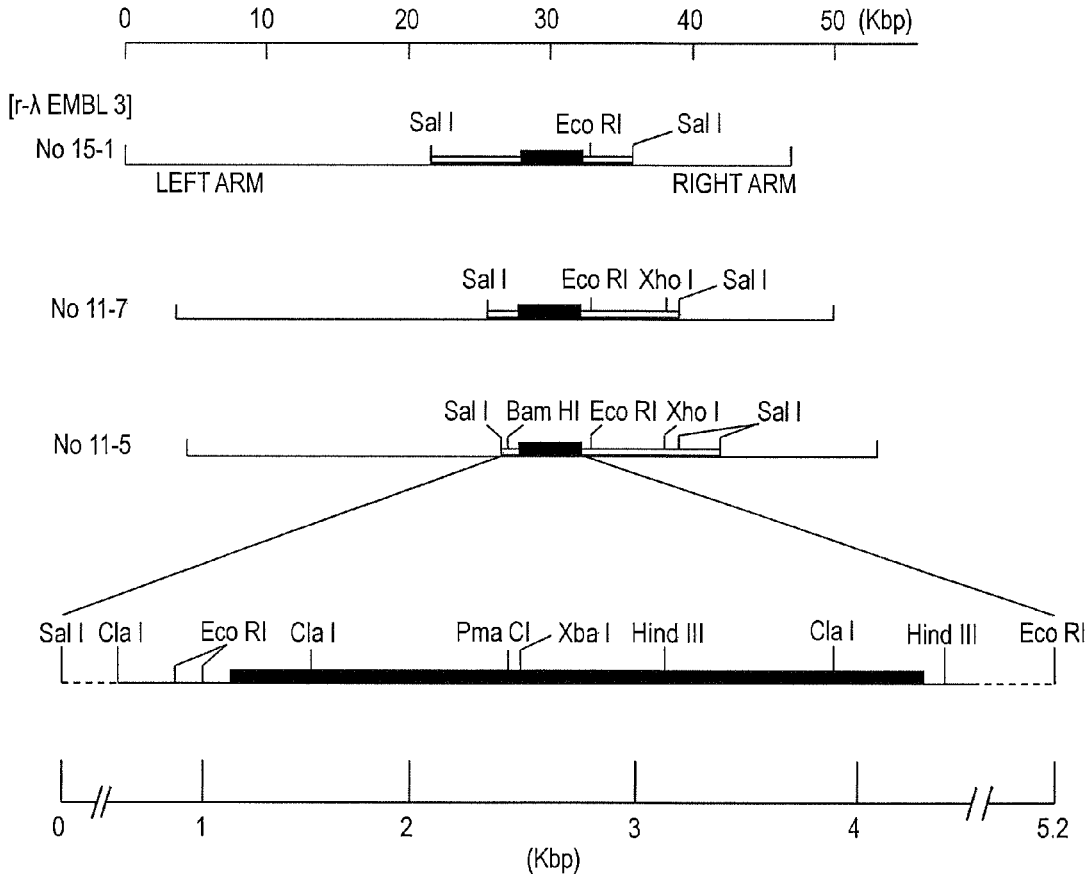

Fig. 1C

Nucleotide sequence of promoter region

5'-CAGACTGCTTATGGCAAATTAACCCCCTCTCTTAATCTTCGTTATTTCAAAGATATTGCAGG

TGACAATGATATCAATCAACGCCACAGCCTTACCTATTTTAATACAGGGGGAAGTACCTTTGA

TATTAAAGGAAATACCGTTGGTGGTGACATTATTAGTGCGGAATTAGGTGCAAATCTCGATAT

-35 -10

CACTCAATCATTAAATT TAGGCA CAACGATGGGCTATCAGCGTTATGACAAA TTTAAT G

TSP SD

Met Pro Ile

AAGGACGCATTGGTTTCACTGTTAGCCAGCGTTTCTA AGGAGA AAAATA ATG CCG ATA

Phe Arg Phe Thr Ala Leu Ala Met Thr Leu Gly Leu Leu Ser Ala Pro

TTT CGT TTT ACT GCA CTT GCA ATG ACA TTG GGG CTA TTA TCA GCG CCT

Mature ChSase

Tyr Asn Ala Met Ala Ala Thr Ser Asn Pro Ala Phe Asp Pro Lys Asn

TAT AAC GCG ATG GCA GCC ACC AGC AAT CCT GCA TTT GAT CCT AAA AAT

Fig. 4

Amended

```
atg ccg ata ttt cgt ttt act gca ctt gca atg aca ttg ggg cta tta     48
Met Pro Ile Phe Arg Phe Thr Ala Leu Ala Met Thr Leu Gly Leu Leu
 1               5                  10                  15
tca gcg cct tat aac gcg atg gca gcc acc agc aat cct gca ttt gat     96
Ser Ala Pro Tyr Asn Ala Met Ala Ala Thr Ser Asn Pro Ala Phe Asp
            20                  25                  30
cct aaa aat ctg atg cag tca gaa att tac cat ttt gca caa aat aac    144
Pro Lys Asn Leu Met Gln Ser Glu Ile Tyr His Phe Ala Gln Asn Asn
        35                  40                  45
cca tta gca gac ttc tca tca gat aaa aac tca ata cta acg tta tct    192
Pro Leu Ala Asp Phe Ser Ser Asp Lys Asn Ser Ile Leu Thr Leu Ser
    50                  55                  60
gat aaa cgt agc att atg gga aac caa tct ctt tta tgg aaa tgg aaa    240
Asp Lys Arg Ser Ile Met Gly Asn Gln Ser Leu Leu Trp Lys Trp Lys
65                  70                  75                  80
ggt ggt agt agc ttt act tta cat aaa aaa ctg att gtc ccc acc gat    288
Gly Gly Ser Ser Phe Thr Leu His Lys Lys Leu Ile Val Pro Thr Asp
                85                  90                  95
aaa gaa gca tct aaa gca tgg gga cgc tca tct acc ccc gtt ttc tca    336
Lys Glu Ala Ser Lys Ala Trp Gly Arg Ser Ser Thr Pro Val Phe Ser
            100                 105                 110
ttt tgg ctt tac aat gaa aaa ccg att gat ggt tat ctt act atc gat    384
Phe Trp Leu Tyr Asn Glu Lys Pro Ile Asp Gly Tyr Leu Thr Ile Asp
        115                 120                 125
ttc gga gaa aaa ctc att tca acc agt gag gct cag gca ggc ttt aaa    432
Phe Gly Glu Lys Leu Ile Ser Thr Ser Glu Ala Gln Ala Gly Phe Lys
    130                 135                 140
gta aaa tta gat ttc act ggc tgg cgt gct gtg gga gtc tct tta aat    480
Val Lys Leu Asp Phe Thr Gly Trp Arg Ala Val Gly Val Ser Leu Asn
145                 150                 155                 160
aac gat ctt gaa aat cga gag atg acc tta aat gca acc aat acc tcc    528
Asn Asp Leu Glu Asn Arg Glu Met Thr Leu Asn Ala Thr Asn Thr Ser
                165                 170                 175
tct gat ggt act caa gac agc att ggg cgt tct tta ggt gct aaa gtc    576
Ser Asp Gly Thr Gln Asp Ser Ile Gly Arg Ser Leu Gly Ala Lys Val
            180                 185                 190
gat agt att cgt ttt aaa gcg cct tct aat gtg agt cag ggt gaa atc    624
Asp Ser Ile Arg Phe Lys Ala Pro Ser Asn Val Ser Gln Gly Glu Ile
        195                 200                 205
tat atc gac cgt att atg ttt tct gtc gat gat gct cgc tac caa tgg    672
Tyr Ile Asp Arg Ile Met Phe Ser Val Asp Asp Ala Arg Tyr Gln Trp
    210                 215                 220
tct gat tat caa gta aaa act cgc tta tca gaa cct gaa att caa ttt    720
Ser Asp Tyr Gln Val Lys Thr Arg Leu Ser Glu Pro Glu Ile Gln Phe
225                 230                 235                 240
cac aac gta aag cca caa cta cct gta aca cct gaa aat tta gcg gcc    768
His Asn Val Lys Pro Gln Leu Pro Val Thr Pro Glu Asn Leu Ala Ala
                245                 250                 255
att gat ctt att cgc caa cgt cta att aat gaa ttt gtc gga ggt gaa    816
Ile Asp Leu Ile Arg Gln Arg Leu Ile Asn Glu Phe Val Gly Gly Glu
            260                 265                 270
aaa gag aca aac ctc gca tta gaa gag aat atc agc aaa tta aaa agt    864
Lys Glu Thr Asn Leu Ala Leu Glu Glu Asn Ile Ser Lys Leu Lys Ser
        275                 280                 285
```

Fig. 7A
Amended

```
gat ttc gat gct ctt aat att cac act tta gca aat ggt gga acg caa    912
Asp Phe Asp Ala Leu Asn Ile His Thr Leu Ala Asn Gly Gly Thr Gln
    290                 295                 300
ggc aga cat ctg atc act gat aaa caa atc att att tat caa cca gag    960
Gly Arg His Leu Ile Thr Asp Lys Gln Ile Ile Ile Tyr Gln Pro Glu
305                 310                 315                 320
aat ctt aac tcc caa gat aaa caa cta ttt gat aat tat gtt att tta   1008
Asn Leu Asn Ser Gln Asp Lys Gln Leu Phe Asp Asn Tyr Val Ile Leu
                325                 330                 335
ggt aat tac acg aca tta atg ttt aat att agc cgt gct tat gtg ctg   1056
Gly Asn Tyr Thr Thr Leu Met Phe Asn Ile Ser Arg Ala Tyr Val Leu
            340                 345                 350
gaa aaa gat ccc aca caa aag gcg caa cta aag cag atg tac tta tta   1104
Glu Lys Asp Pro Thr Gln Lys Ala Gln Leu Lys Gln Met Tyr Leu Leu
        355                 360                 365
atg aca aag cat tta tta gat caa ggc ttt gtt aaa ggg agt gct tta   1152
Met Thr Lys His Leu Leu Asp Gln Gly Phe Val Lys Gly Ser Ala Leu
    370                 375                 380
gtg aca acc cat cac tgg gga tac agt tct cgt tgg tgg tat att tcc   1200
Val Thr Thr His His Trp Gly Tyr Ser Ser Arg Trp Trp Tyr Ile Ser
385                 390                 395                 400
acg tta tta atg tct gat gca cta aaa gaa gcg aac cta caa act caa   1248
Thr Leu Leu Met Ser Asp Ala Leu Lys Glu Ala Asn Leu Gln Thr Gln
                405                 410                 415
gtt tat gat tca tta ctg tgg tat tca cgt gag ttt aaa agt agt ttt   1296
Val Tyr Asp Ser Leu Leu Trp Tyr Ser Arg Glu Phe Lys Ser Ser Phe
            420                 425                 430
gat atg aaa gta agt gct gat agc tct gat cta gat tat ttc aat acc   1344
Asp Met Lys Val Ser Ala Asp Ser Ser Asp Leu Asp Tyr Phe Asn Thr
        435                 440                 445
tta tct cgc caa cat tta gcc tta tta tta cta gag cct gat gat caa   1392
Leu Ser Arg Gln His Leu Ala Leu Leu Leu Leu Glu Pro Asp Asp Gln
    450                 455                 460
aag cgt atc aac tta gtt aat act ttc agc cat tat atc act ggc gca   1440
Lys Arg Ile Asn Leu Val Asn Thr Phe Ser His Tyr Ile Thr Gly Ala
465                 470                 475                 480
tta acg caa gtg cca ccg ggt ggt aaa gat ggt tta cgc cct gat ggt   1488
Leu Thr Gln Val Pro Pro Gly Gly Lys Asp Gly Leu Arg Pro Asp Gly
                485                 490                 495
aca gca tgg cga cat gaa ggc aac tat ccg ggc tac tct ttc cca gcc   1536
Thr Ala Trp Arg His Glu Gly Asn Tyr Pro Gly Tyr Ser Phe Pro Ala
            500                 505                 510
ttt aaa aat gcc tct cag ctt att tat tta tta cgc gat aca cca ttt   1584
Phe Lys Asn Ala Ser Gln Leu Ile Tyr Leu Leu Arg Asp Thr Pro Phe
        515                 520                 525
tca gtg ggt gaa agt ggt tgg aat aac ctg aaa aaa gcg atg gtt tca   1632
Ser Val Gly Glu Ser Gly Trp Asn Asn Leu Lys Lys Ala Met Val Ser
    530                 535                 540
gcg tgg atc tac agt aat cca gaa gtt gga tta ccg ctt gca gga aga   1680
Ala Trp Ile Tyr Ser Asn Pro Glu Val Gly Leu Pro Leu Ala Gly Arg
545                 550                 555                 560
cac cct ttt aac tca cct tcg tta aaa tca gtc gct caa ggc tat tac   1728
His Pro Phe Asn Ser Pro Ser Leu Lys Ser Val Ala Gln Gly Tyr Tyr
                565                 570                 575
tgg ctt gcc atg tct gca aaa tca tcg cct gat aaa aca ctt gca tct   1776
Trp Leu Ala Met Ser Ala Lys Ser Ser Pro Asp Lys Thr Leu Ala Ser
```

Fig. 7B

Amended

```
            580                 585                 590
att tat ctt gcg att agt gat aaa aca caa aat gaa tca act gct att    1824
Ile Tyr Leu Ala Ile Ser Asp Lys Thr Gln Asn Glu Ser Thr Ala Ile
        595                 600                 605
ttt gga gaa act att aca cca gcg tct tta cct caa ggt ttc tat gcc    1872
Phe Gly Glu Thr Ile Thr Pro Ala Ser Leu Pro Gln Gly Phe Tyr Ala
    610                 615                 620
ttt aat ggc ggt gct ttt ggt att cat cgt tgg caa gat aaa atg gtg    1920
Phe Asn Gly Gly Ala Phe Gly Ile His Arg Trp Gln Asp Lys Met Val
625                 630                 635                 640
aca ctg aaa gct tat aac acc aat gtt tgg tca tct gaa att tat aac    1968
Thr Leu Lys Ala Tyr Asn Thr Asn Val Trp Ser Ser Glu Ile Tyr Asn
                645                 650                 655
aaa gat aac cgt tat ggc cgt tac caa agt cat ggt gtc gct caa ata    2016
Lys Asp Asn Arg Tyr Gly Arg Tyr Gln Ser His Gly Val Ala Gln Ile
            660                 665                 670
gtg agt aat ggc tcg cag ctt tca cag ggc tat cag caa gaa ggt tgg    2064
Val Ser Asn Gly Ser Gln Leu Ser Gln Gly Tyr Gln Gln Glu Gly Trp
        675                 680                 685
gat tgg aat aga atg caa ggg gca acc act att cac ctt cct ctt aaa    2112
Asp Trp Asn Arg Met Gln Gly Ala Thr Thr Ile His Leu Pro Leu Lys
    690                 695                 700
gac tta gac agt cct aaa cct cat acc tta atg caa cgt gga gag cgt    2160
Asp Leu Asp Ser Pro Lys Pro His Thr Leu Met Gln Arg Gly Glu Arg
705                 710                 715                 720
gga ttt agc gga aca tca tcc ctt gaa ggt caa tat ggc atg atg gca    2208
Gly Phe Ser Gly Thr Ser Ser Leu Glu Gly Gln Tyr Gly Met Met Ala
                725                 730                 735
ttc gat ctt att tat ccc gcc aat ctt gag cgt ttt gat cct aat ttc    2256
Phe Asp Leu Ile Tyr Pro Ala Asn Leu Glu Arg Phe Asp Pro Asn Phe
            740                 745                 750
act gcg aaa aag agt gta tta gcc gct gat aat cac tta att ttt att    2304
Thr Ala Lys Lys Ser Val Leu Ala Ala Asp Asn His Leu Ile Phe Ile
        755                 760                 765
ggt agc aat ata aat agt agt gat aaa aat aaa aat gtt gaa acg acc    2352
Gly Ser Asn Ile Asn Ser Ser Asp Lys Asn Lys Asn Val Glu Thr Thr
    770                 775                 780
tta ttc caa cat gcc att act cca aca tta aat acc ctt tgg att aat    2400
Leu Phe Gln His Ala Ile Thr Pro Thr Leu Asn Thr Leu Trp Ile Asn
785                 790                 795                 800
gga caa aag ata gaa aac atg cct tat caa aca aca ctt caa caa ggt    2448
Gly Gln Lys Ile Glu Asn Met Pro Tyr Gln Thr Thr Leu Gln Gln Gly
                805                 810                 815
gat tgg tta att gat agc aat ggc aat ggt tac tta att act caa gca    2496
Asp Trp Leu Ile Asp Ser Asn Gly Asn Gly Tyr Leu Ile Thr Gln Ala
            820                 825                 830
gaa aaa gta aat gta agt cgc caa cat cag gtt tca gcg gaa aat aaa    2544
Glu Lys Val Asn Val Ser Arg Gln His Gln Val Ser Ala Glu Asn Lys
        835                 840                 845
aat cgc caa ccg aca gaa gga aac ttt agc tcg gca tgg atc gat cac    2592
Asn Arg Gln Pro Thr Glu Gly Asn Phe Ser Ser Ala Trp Ile Asp His
    850                 855                 860
agc act cgc ccc aaa gat gcc agt tat gag tat atg gtc ttt tta gat    2640
Ser Thr Arg Pro Lys Asp Ala Ser Tyr Glu Tyr Met Val Phe Leu Asp
865                 870                 875                 880
gcg aca cct gaa aaa atg gga gag atg gca caa aaa ttc cgt gaa aat    2688
```

Fig. 7C

Amended

```
Ala Thr Pro Glu Lys Met Gly Glu Met Ala Gln Lys Phe Arg Glu Asn
                885                 890                 895
aat ggg tta tat cag gtt ctt cgt aag gat aaa gac gtt cat att att    2736
Asn Gly Leu Tyr Gln Val Leu Arg Lys Asp Lys Asp Val His Ile Ile
            900                 905                 910
ctc gat aaa ctc agc aat gta acg gga tat gcc ttt tat cag cca gca    2784
Leu Asp Lys Leu Ser Asn Val Thr Gly Tyr Ala Phe Tyr Gln Pro Ala
        915                 920                 925
tca att gaa gac aaa tgg atc aaa aag gtt aat aaa cct gca att gtg    2832
Ser Ile Glu Asp Lys Trp Ile Lys Lys Val Asn Lys Pro Ala Ile Val
    930                 935                 940
atg act cat cga caa aaa gac act ctt att gtc agt gca gtt aca cct    2880
Met Thr His Arg Gln Lys Asp Thr Leu Ile Val Ser Ala Val Thr Pro
945                 950                 955                 960
gat tta aat atg act cgc caa aaa gca gca act cct gtc acc atc aat    2928
Asp Leu Asn Met Thr Arg Gln Lys Ala Ala Thr Pro Val Thr Ile Asn
                965                 970                 975
gtc acg att aat ggc aaa tgg caa tct gct gat aaa aat agt gaa gtg    2976
Val Thr Ile Asn Gly Lys Trp Gln Ser Ala Asp Lys Asn Ser Glu Val
            980                 985                 990
aaa tat cag gtt tct ggt gat aac act gaa ctg acg ttt acg agt tac    3024
Lys Tyr Gln Val Ser Gly Asp Asn Thr Glu Leu Thr Phe Thr Ser Tyr
        995                 1000                1005
ttt ggt att cca caa gaa atc aaa ctc tcg cca ctc cct tga            3066
Phe Gly Ile Pro Gln Glu Ile Lys Leu Ser Pro Leu Pro
    1010                1015                1020
```

Fig. 7D
Amended

GENE ENCODING CHONDROITINASE ABC AND USES THEREFOR

Matter enclosed in heavy brackets [ ] appears in the original patent but forms no part of this reissue specification; matter printed in italics indicates the additions made by reissue.

This application is a continuation of application Ser. No. 08/184,435 filed on Jan. 14, 1994 now abandoned Entitled: Gene Encoding Chondroitinase ABC And Uses Therefor, which is a divisional of Ser. No. 08/074,349 filed Jun. 8, 1993 now abandoned.

BACKGROUND OF THE INVENTION

Chondroitin lyase (EC 4.2.2.4) or chondroitinase ABC is an enzyme which catalyzes the depolymerization of chondroitin sulfate. Through β-elimination of 1,4 hexosaminidic bonds, chondroitinase ABC degrades chondroitin, chondroitin 4-sulfate (chondroitin A sulfate), dermatan sulfate (chondroitin B sulfate), chondroitin 6-sulfate (chondroitin C sulfate) and hyaluronate to the respective unsaturated disaccharides (Δdi-OS for chondroitin, Δdi-4S for chondroitin A sulfate, Δdi-4-6S for chondroitin B sulfate and Δdi-6S for chondroitin C sulfate, respectively). The enzyme has been isolated in various strains of bacteria (Neuberg, C. et al., (1914) Biochem. Z. 67: 82-89) (Neuberg, C. et al. (1931) Biochem, Z. 234: 345-346; Yamagata, T. et al., (1968) J. Biol. Chem. 243: 1523-1535) including Proteus vulgaris (Yamagata, T. et al. (1968) J. Biol. Chem. 243: 1523-1535; Thurston, C. F. (1974) J. Gen. Microbiol. 80: 515-522; Sato N. et al. (1986) Agric. Biol. Chem. 50: 1057-1059; Sato N. et al. (1986) Biotechnol. Bioeng. 28: 1707-1712; Sato, N. et al. (1986) J. Ferment. Technol. 64: 155-159).

Chondroitin sulfate consists of alternating β 1-3 glucuronidic and β 1-4 N-acetylgalactosaminidic bonds, and is sulfated at either C-4 or C-6 of the N-acetylgalactosamine pyranose. Chondroitin sulfate is known to be widely distributed in mammalian tissue, such as in skin, cornea, bone and especially in cartilage. Thus, chondroitinase ABC has been used as an experimental reagent for the determination or quantitation of total amount of galactosaminoglycans in the field of orthopedic surgery (Linker, A. et al. (1960) J. Biol. Chem. 235: 3061-3065; Saito, H. et al. (1968) J. Biol. Chem. 243: 1536-1542; Pettipher, E. R. et al. (1989) Arthritis Rheum. 32: 601-607; Caterson, B. et al. (1990) J. Cell Science 97: 411-417; and Seibel, M. J. et al. (1992) Arch. Biochem. Biophys. 296: 410-418).

Recently, chondroitinase ABC has been reported to be a potential reagent for chemonucleolysis, an established treatment for intervertebral disc displacement (Kato, F. et al. (1990) Clin. Orthop. 253: 301-308; Henderson, N. et al. (1991) Spine 16: 203-209). However, for the utilization of chondroitinase ABC as a clinical reagent, there are many problems to be overcome. For example, the preparation of chondroitinase ABC from P. vulgaris requires tedious and intricate procedures, since the cellular content of the enzyme is low. Therefore, an efficient method for the efficient preparation of highly purified chondroitinase ABC is now sought.

SUMMARY OF THE INVENTION

This invention pertains to nucleic acid sequences coding for the chondroitinase ABC gene and isolated chondroitinase ABC protein produced in a host cell transformed with a nucleic acid vector directing the expression of a nucleotide sequence coding for chondroitinase ABC. Chondroitinase ABC prepared by chemical synthesis is also provided. This invention further provides monoclonal and polyclonal antibodies which are specifically reactive with chondroitinase ABC. The isolated chondroitinase ABC can be used in methods of treating intervertebral disc displacement and promoting neurite regeneration or in method of detecting the presence of galactosaminoglycans.

BRIEF DESCRIPTION OF THE DRAWINGS

FIGS. 1-A and 1-B show the primers used for polymerase chain reaction (PCR) amplification of chondroitinase ABC from P. vulgaris genomic DNA[;]. *FIG. 1A provides the amino acid sequence of the N-terminal region of purified chondroitinase ABC (SEQ ID NO: 3), the nucleotide sequences of the sense primers (SEQ ID NOS 5 and 6), and the nucleotide sequences of the antisense primers (SEQ ID NOS 7 and 8).*

FIG. 1-B also shows the probe used for plaque hybridization[;]. *FIG. 1B provides the amino acid sequence of the N-terminal region of purified chondroitinase ABC (SEQ ID NO: 3), the nucleotide sequence of primer A (SEQ ID NO: 10), the nucleotide sequence of the probe (SEQ ID NO: 9), the nucleotide sequence of primer B (SEQ ID NO: 11), and the full length DNA sequences (SEQ ID NOS 12 and 13).*

FIG. 1-C shows the restriction maps for three recombinant phages and the fragment of phage 11-5 which was subcloned into pSTV29 for sequencing.

FIG. 4 shows the nucleotide sequence of the promoter region of chondroitinase ABC (SEQ ID NO: 16) and the peptide sequence (SEQ ID NO:17).

FIG. 7 shows the DNA (SEQ ID NO:1) and amino acid sequence (SEQ ID NO:2) of the chondroitinase ABC gene[including non-coding regions].

DETAILED DESCRIPTION OF THE INVENTION

Figure 2:
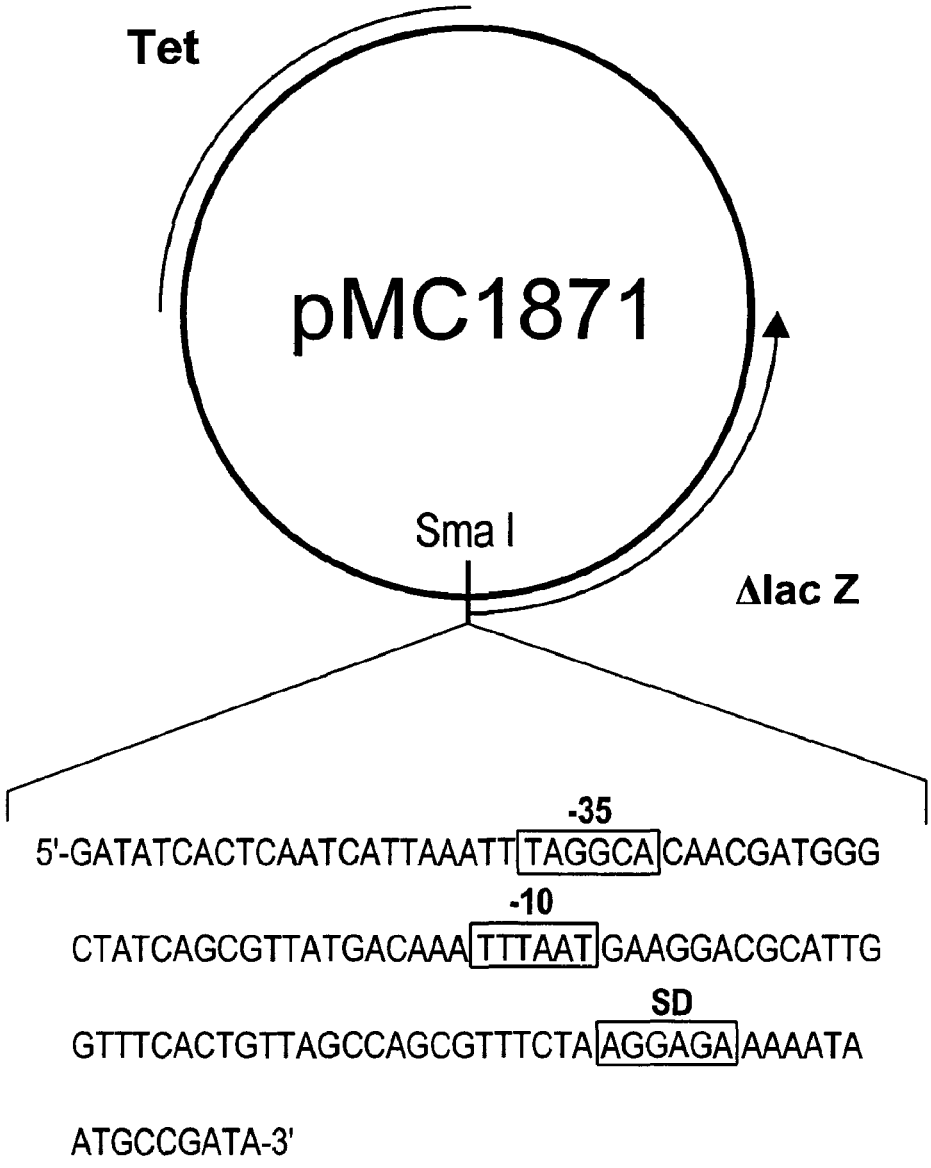
FIG. 2 shows the construction of pCHSP, a hybrid plasmid containing the putative promoter region of chondroitinase ABC (SEQ ID NO: 14).

This invention pertains to nucleic acid sequences coding for chondroitinase ABC, an enzyme which degrades chondroitin A, B, and C. The chondroitinase ABC gene was derived using recombinant DNA techniques. A nucleic acid sequence coding for chondroitinase ABC preferably has the sequence shown in SEQ ID NO: 1 (FIG. 7). The deduced amino acid sequence of chondroitinase ABC is shown in SEQ ID NO:2 (FIG. 7).

Accordingly, one aspect of the invention pertains to an isolated nucleic acid having a nucleotide sequence coding for chondroitinase ABC, fragments thereof, or equivalents thereof. The term nucleic acid as used herein is intended to include such fragments or equivalents. A nucleic acid sequence coding for chondroitinase ABC can obtained from mRNA present in Proteus vulgaris. Nucleic acid sequences coding for chondroitinase ABC can also be obtained from P. vulgaris genomic DNA. The nucleic acid sequence coding for chondroitinase ABC can be obtained using the method disclosed herein or any other suitable technique for isolation and molecular cloning of genes. The nucleic acid sequences of the invention can be DNA or RNA. The preferred nucleic acid is a DNA having the sequence depicted in SEQ ID NO:1 (FIG. 7) or equivalents thereof.

The term equivalent is intended to include nucleotide sequences coding for functionally equivalent chondroitinase ABC proteins. For example, DNA sequence polymorphisms within the nucleotide sequence of chondroitinase ABC (especially those within the third base of a codon) may result in "silent" mutations which do not affect the amino acid sequence of the chondroitinase ABC protein. However, it is expected that DNA sequence polymorphisms that do lead to changes in the amino acid sequence of chondroitinase ABC will exist. It will be appreciated by one skilled in the art that these variations in one or more nucleotides (up to about 3-4% of the nucleotides) of the nucleic acid sequence coding for chondroitinase ABC may exist due to natural allelic variation. Any and all such nucleotide variations and resulting amino acid polymorphisms are within the scope of the invention. Furthermore, there may be one or more isoforms or related, cross-reacting family members of chondroitinase ABC. Such isoforms or family members are defined as proteins related in function and amino acid sequence to chondroitinase ABC, but encoded by genes at different loci.

A fragment of the nucleic acid sequence coding for chondroitinase ABC is defined as a nucleotide sequence having fewer nucleotides than the nucleotide sequence coding for the entire amino acid sequence of chondroitinase ABC protein. Such fragments encode a catalytically-active fragment of chondroitinase ABC protein which depolymerizes chondroitin A, B, or C. Nucleic acid fragments within the scope of the invention include those capable of hybridizing with nucleic acid from other animal species for use in screening protocols to detect chondroitinase ABC or enzymes that are cross-reactive with chondroitinase ABC. Nucleic acid sequences within the scope of the invention may also contain linker sequences, modified restriction endonuclease sites and other sequences useful for molecular cloning, expression or purification of recombinant chondroitinase ABC or catalytically-active fragments thereof.

This invention also provides expression vectors containing a nucleic acid sequence coding for chondroitinase ABC, operably linked to at least one regulatory sequence. Operably linked is intended to mean that the nucleotide sequence is linked to a regulatory sequence in a manner which allows expression of the nucleotide sequence. Regulatory sequences are art-recognized and are selected to direct expression of chondroitinase ABC. Accordingly, the term regulatory sequence includes promoters, enhancers and other expression control elements. Such regulatory sequences are described in Goeddel, Gene Expression Technology: Methods in Enzymology 185, Academic Press, San Diego, Calif. (1990). It should be understood that the design of the expression vector may depend on such factors as the choice of the host cell to be transformed and/or the type of protein desired to be expressed.

This invention further pertains to a host cell transformed to express chondroitinase ABC. The host cell may be any prokaryotic or eukaryotic cell. For example, chondroitinase ABC protein may be expressed in bacterial cells such as E. coli, insect cells (baculovirus), yeast, or mammalian cells such as Chinese hamster ovary cells (CHO). Other suitable host cells may be found in Goeddel, (1990) supra or one known to those skilled in the art.

Expression in eukaryotic cells such as mammalian, yeast, or insect cells can lead to partial or complete glycosylation and/or formation of relevant inter- or intra-chain disulfide bonds of recombinant protein. Examples of vectors for expression in yeast S. cerivisae include pYepSec1 (Baldari. et al., (1987) EMBO J. 6:229-234), pMFa (Kurjan and Herskowitz, (1982) Cell 30:933-943), pJRY88 (Schultz et al., (1987) Gene 54:113-123), and pYES2 (Invitrogen Corporation, San Diego, Calif.). Baculovirus vectors available for expression of proteins in cultured insect cells (SF 9 cells) include the pAc series (Smith et al., (1983) Mol. Cell Biol. 3:2156-2165) and the pVL series (Lucklow, V. A., and Summers, M. D., (1989) Virology 170:31-39). Generally COS cells (Gluzman, Y., (1981) Cell 23:175-182) are used in conjunction with such vectors as pCDM 8 (Aruffo, A. and Seed, B., (1987) Proc. Natl. Acad. Sci. USA 84:8573-8577) for transient amplification/expression in mammalian cells, while CHO ($dhfr^-$ Chinese Hamster Ovary) cells are used with vectors such as pMT2PC (Kaufman et al. (1987), EMBO J. 6:187-195) for stable amplification/expression in mammalian cells. Vector DNA can be introduced into mammalian cells via conventional techniques such as calcium phosphate or calcium chloride co-precipitation, DEAE-dextran-mediated transfection, or electroporation. Suitable methods for transforming host cells can be found in Sambrook et al, Molecular Cloning: A Laboratory Manual, 2nd Edition, Cold Spring Harbor Laboratory press (1989), and other laboratory textbooks.

Expression in prokaryotes is most often carried out in E. coli with either fusion or non-fusion inducible expression vectors. Fusion vectors usually add a number of $NH_2$ terminal amino acids to the expressed target gene. These $NH_2$ terminal amino acids often are referred to as a reporter group. Such reporter groups usually serve two purposes: 1) to increase the solubility of the target recombinant protein; and 2) to aid in the purification of the target recombinant protein by acting as a ligand in affinity purification. Often, in fusion expression vectors, a proteolytic cleavage site is introduced at the junction of the reporter group and the target recombinant protein to enable separation of the target recombinant protein from the reporter group subsequent to purification of the fusion protein. Such enzymes include Factor Xa, thrombin and enterokinase. Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-tranferase, maltose E binding protein, or protein A, respectively, to the target recombinant protein.

Inducible non-fusion expression vectors include pTrc (Amann et al., (1988) Gene 69:301-315) and pET 11d (Studier et al., Gene Expression Technology: Methods in Enzymology 185, Academic Press, San Diego, Calif. (1990) 60-89). While target gene expression relies on host RNA polymerase transcription from the hybrid trp-lac fusion promoter in pTrc, expression of target genes inserted into pET 11d relies on transcription from the T7 gn10-lac 0 fusion promoter mediated by coexpressed viral RNA polymerase (T7 gn1). This viral polymerase is supplied by host strains BL21(DE3) or HMS174(DE3) from a resident g prophage harboring a T7 gn1 under the transcriptional control of the lacUV 5 promoter.

One strategy to maximize recombinant chondroitinase ABC expression in E. coli is to express the protein in a host bacteria with an impaired capacity to proteolytically cleave the recombinant protein (Gottesman, S., Gene Expression Technology: Methods in Enzymology 185, Academic Press, San Diego, Calif. (1990) 119-128). Another strategy would be to alter the nucleic acid sequence of the chondroitinase ABC gene to be inserted into an expression vector so that the individual codons for each amino acid would be those preferentially utilized in highly expressed E. coli proteins (Wada et al., (1992) Nuc. Acids Res. 20:2111-2118). Such alteration of nucleic acid sequences of the invention can be carried out by standard DNA synthesis techniques.

The nucleic acid sequences of the invention can also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071, incorporated by reference herein).

This invention further pertains to methods of producing chondroitinase ABC protein. For example, a host cell transformed with a nucleic acid vector directing expression of a nucleotide sequence coding for chondroitinase ABC protein can be cultured under appropriate conditions to allow expression of chondroitinase ABC to occur. The protein may be secreted and isolated from a mixture of cells and medium containing chondroitinase ABC protein. Alternatively, the protein may be retained cytoplasmically and the cells harvested, lysed and the protein isolated. The culture includes host cells, media and other byproducts. Suitable mediums for cell culture are well known in the art. Chondroitinase ABC protein can be isolated from cell culture medium, host cells, or both using techniques known in the art for purifying proteins including ion-exchange chromatography, gel filtration chromatography, ultrafiltration, electrophoresis, and immunoaffinity purification with antibodies specific for chondroitinase ABC or fragment thereof.

Another aspect of the invention pertains to isolated chondroitinase ABC protein. The term "chondroitinase ABC" or "chondroitinase ABC protein" is intended to include functional equivalents thereof and catalytically-active fragments thereof. The term functional equivalent is intended to include proteins which differ in amino acid sequence from the chondroitinase ABC sequence depicted in SEQ ID NO:2 (FIG. 7) but where such differences result in a modified protein which functions in the same or similar manner as chondroitinase ABC or which has the same or similar characteristics of chondroitinase ABC. For example, a functional equivalent of chondroitinase ABC may have a modification such as a substitution, addition or deletion of an amino acid residue which is not directly involved in the enzyme activity of chondroitinase ABC (i.e., the ability of chondroitinase ABC to depolymerize chondroitin 4-sulphate, chondroitin 6-sulfate, and dermatan sulfate). Various modifications of the chondroitinase ABC protein to produce functional equivalents of chondroitinase ABC are described in detail herein.

The term isolated as used herein refers to chondroitinase ABC protein substantially free of cellular material or culture medium when produced by recombinant DNA techniques, or chemical precursors or other chemicals when chemically synthesized. Such chondroitinase ABC protein is also characterized as being essentially free of all other P. vulgaris proteins. Accordingly, an isolated chondroitinase ABC protein is produced recombinantly or synthetically and is substantially free of cellular material and culture medium or substantially free of chemical precursors or other chemicals and is essentially free of all other P. vulgaris proteins.

Fragments of chondroitinase ABC which depolymerize chondroitin A, B, or C (referred to herein as catalytically-active fragments) may be obtained, for example, by screening peptides recombinantly produced from the corresponding fragment of the nucleic acid sequence of chondroitinase ABC coding for such peptides. In addition, fragments can be chemically synthesized using techniques known in the art such as by conventional Merrifield solid phase f-Moc or t-Boc chemistry. For example, the chondroitinase ABC protein may be arbitrarily divided into fragments of desired length. The fragments can be produced (recombinantly or by chemical synthesis) and tested to determine their enzymatic activity, for example, by contacting the fragment with chondroitin A, B, or C under conditions which allow for depolymerization and determining the extent to which depolymerization occurs.

It is possible to modify the structure of the chondroitinase ABC protein for such purposes as increasing solubility, enhancing therapeutic efficacy, or stability (e.g., shelf life ex vivo and resistance to proteolytic degradation in vivo). Such modified proteins or analogues are considered functional equivalents of the chondroitinase ABC protein as defined herein.

To facilitate purification and potentially increase solubility of the chondroitinase ABC protein, it is possible to add an amino acid reporter group to the protein backbone. For example, hexa-histidine can be added to the protein for purification by immobilized metal ion affinity chromatography (Hochuli, E. et al., (1988) Bio/Technology 6:1321-1325). In addition, to facilitate isolation of chondroitinase ABC protein free of irrelevant sequences, specific endoprotease cleavage sites can be introduced between the sequences of the reporter group and the protein or peptide.

Another aspect of the invention pertains to an antibody specifically reactive with chondroitinase ABC. The antibodies of this invention can be used to isolate the naturally-occurring or native form of chondroitinase ABC or to neutralize the enzyme so that it is unable to depolymerize chondroitin. For example, by using isolated chondroitinase ABC protein based on the cDNA sequence of chondroitinase ABC, anti-protein/anti-peptide antisera or monoclonal antibodies can be made using standard methods. A mammal such as a mouse, a hamster or a rabbit can be immunized with an immunogenic form of the isolated chondroitinase ABC protein (e.g., chondroitinase ABC protein or an antigenic fragment which is capable of eliciting an antibody response). Techniques for conferring immunogenicity on a protein or peptide include conjugation to carriers or other techniques well known in the art. The chondroitinase ABC protein or fragment thereof can be administered in the presence of adjuvant. The progress of immunization can be monitored by detection of antibody titers in plasma or serum standard ELISA or other immunoassay can be used with the immunogen as antigen to assess the levels of antibodies.

Following immunization, anti-chondroitinase ABC antisera can be obtained and, if desired, polyclonal anti-chondroitinase ABC antibodies isolated from the serum. To produce monoclonal antibodies, antibody producing cells (lymphocytes) can be harvested from an immunized animal and fused by standard somatic cell fusion procedures with immortalizing cells such as myeloma cells to yield hybridoma cells. Such techniques are well known in the art, for example the hybridoma technique originally developed by Kohler and Milstein, Nature (1975) 256:495-497, as well as other techniques such as the human B-cell hybridoma technique (Kozbar et al., Immunology Today (1983) 4:72) and the EBV-hybridoma technique to produce human monoclonal antibodies (Cole et al., Monoclonal Antibodies and Cancer Therapy (1985) Alan R. Liss, Inc. pp. 77-96). Hybridoma cells can be screened immunochemically for production of antibodies specifically reactive with the chondroitinase ABC protein and the monoclonal antibodies isolated.

The term antibody as used herein is intended to include fragments thereof which are also specifically reactive with the chondroitinase ABC protein or fragment thereof. Antibodies can be fragmented using conventional techniques and the fragments screened for utility in the same manner as described above for whole antibodies. For example, $F(ab')_2$ fragments can be generated by treating the antibody with pepsin. The resulting $F(ab')_2$ fragment can be treated with papain to reduce disulfide bridges to produce Fab' fragments. The antibody of the present invention is further intended to include bispecific and chimeric molecules having an anti-chondroitinase ABC portion.

This invention provides therapeutic compositions for the treatment of intervertebral displacement or nerve damage. The composition comprises a therapeutically active amount of chondroitinase ABC protein and a pharmaceutically acceptable carrier. Administration of the therapeutic compositions of the present invention to an individual to be treated can be carried out using known procedures, at dosages and for periods of time effective to depolymerize chondroitin A, B, or C. A therapeutically active amount of chondroitinase ABC protein may vary according to factors such as the amount of chondroitin to be eliminated, the age, sex, and weight of the individual, and the ability of the chondroitinase ABC protein to depolymerize the chondroitin. Dosage regima may be adjusted to provide the optimum therapeutic response.

The active compound (i.e., chondroitinase ABC protein) may be administered in a convenient manner such as by injection (subcutaneous, intravenous, etc.). If the active compound is administered by injection, for example, about 100 units of active compound (i.e., chondroitinase ABC protein) per dosage unit may be administered to treat intervertebral disc displacement. One unit is the amount of enzyme needed to mediate the release of one micromole of 4,5 unsaturated disaccharide from a substrate of chondroitin C sulfate per minute at 37° C., pH 6.0.

The active compound may be administered parenterally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate or gelatin.

Sterile injectable solutions can be prepared by incorporating active compound (i.e., chondroitinase ABC protein) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., protein) plus any additional desired ingredient from a previously sterile-filtered solution thereof.

As used herein "pharmaceutically acceptable carrier" includes any and all solvents, dispersion media, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic composition is contemplated. Supplementary active compounds can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the elimination of chondroitin A, B, or C.

Isolated chondroitinase ABC protein (i.e., chondroitinase ABC produced recombinantly or by chemical synthesis) is essentially free of all other P. vulgaris proteins. Such protein is of a consistent, well-defined composition and biological activity for use in preparations which can be administered for therapeutic purposes (e.g., to treat intervertebral disc displacement). Such proteins can also be used as diagnostic reagents or in the study of the mechanism of chondroitinase ABC and to design modified derivatives or analogs useful in the depolymerization of chondroitin.

This invention also provides a method of treating intervertebral disc displacement by chemonucleolysis using isolated chondroitinase ABC. Chondroitinase ABC is a particularly useful enzyme for the selective chemonucleolysis of the nucleus pulposus (See, for example, U.S. Pat. No. 4,696,816). The nucleus pulposus is made up of proteoglycans and collagen fibers. Chondroitinase ABC attacks the polysaccharide side chains of the proteoglycans and reduces the swelling of the disc without affecting the structural collagen components or degrading the protein element of the proteoglycan. The disc then shrinks and pressure on the spinal cord is relieved. Thus, to treat intervertebral disc displacement, an active amount of the chondroitinase ABC protein of the invention can be applied to the affected area. For example, 100 units of isolated chondroitinase ABC can be injected into the center of a disc by the standard technique of intradiscal injection (Brown, Intradiscal Therapy, Year Book Medical Publishers, Inc., Chicago, 1983).

The invention further provides a method of treating nerve damage by applying an active amount of the chondroitinase ABC protein of the invention to the affected area to degrade chondroitin-6-sulfate proteoglycans. It has been found that chondroitin 6-sulfate proteoglycans inhibit regeneration of neurites in the adult vertebrate central nervous system (McKeon et al., J. Neurosci 11:3398-3411 (1991)). By removing chondroitin 6-sulfate proteoglycans from the point of injury, it is possible to promote neurite regeneration. For example, a therapeutically effective amount of isolated chondroitinase ABC can be applied to the point of injury in an individual to degrade inhibitory chondroitin 6-sulfate proteoglycans. More than one dose may be administered as indicated by the exigencies of the therapeutic situation.

The chondroitinase ABC protein of the invention can also be used as a diagnostic reagent for detecting the presence of a galactosaminoglycan, such as chondroitin sulfate. For example, the chondroitinase ABC protein can be used as a reagent for determining or quantitating the amount of galactosaminoglycan in a mammalian tissue, such as skin, cornea, bone or cartilage (See e.g., Linker, A. et al. (1960) J. Biol. Chem. 235: 3061-3065; Saito, H. et al. (1968) J. Biol. Chem. 243: 1536-1542; Pettipher, E. R. et al. (1989) Arthritis Rheum. 32: 601-607; Caterson, B. et al. (1990) J. Cell Science 97: 411-417; and Seibel, M. J. et al. (1992) Arch. Biochem. Biophys. 296: 410-418). To determine the presence of chondroitin sulfate in a mammalian tissue, chondroitinase ABC protein can be contacted with a sample of the tissue and the presence or amount of chondroitin sulfate determined using methods well known in the art.

The invention is further illustrated by the following examples which should not be construed as further limiting the subject invention. The contents of all references and published patent applications cited throughout this application are hereby incorporated by reference. The following methods and materials were used throughout the examples discussed below.

Materials and Methods

Bacterial strains, plasmid and phage P. vulgaris IFO3988 was provided by the Institute for Fermentation, Osaka, Japan. E. coli P2392 (hsdR514($r^{k-}$, $m^{k+}$), supE44, supF58, lacY1 or (lacIZY), galT22, metB1, trpR55, (P2)) was used as the lysogen for P2 phage. EMBL3 vector was purchased from Toyobo Co., Ltd., Japan. PCR products were ligated with pT7 Blue T-vector(Takara Shuzo Co., Ltd., Japan). E. coli JM109 (recA1, endA1, gyrA96, thi, hsdR17($r^{k-}$, $m^{k+}$), supE44, relA1, λ-, Δ(lac-proB), (F', proAB, lacIq M15, traD36) was used as the host strain for pMC1871 promoter selection vector (Pharmacia LKB, Japan). E. coli XL1-Blue(endA1, hsdR17($r^{k-}$, $m^{k+}$), supE44, thi-1, recA1, gyrA96, relA1, A(lac), (F', proAB, lac, (lacZΔM15, Tn10(tetr)) (Int'l Dep. No. FERM BP-4170). E. coli XL1-Blue is a host cell for both pSTV28, and pSTV29 (Takara Shuzo Co., Ltd., Japan).

N-terminal amino acid sequence Chondroitinase ABC was purified as described previously (Sato, N. et al. (1986) Agric. Biol. Chem. 50: 1057-1059). The N-terminal amino acid sequence of chondroitinase ABC was sequenced by automatic Edman degradation on a gas-phase sequencer (Applied Biosystem, Foster, Calif.). The sequence of the N-terminal region of chondroitinase ABC was Ala-Thr-Ser-Asn-Pro-Ala-Phe-Asp-Pro-Lys-Asn-Leu-Met-Gln-Ser-Glu-Ile-Tyr (18 amino acid residues) (SEQ ID NO:3) The double stranded DNA sequence is shown in FIG. 1-B (SEQ ID NOS:12-13).

Isolation of DNA and synthesis of nucleic acid, primer, and probe Isolation of chromosomal DNA of P. vulgaris was carried out by the standard method (Silhavy, T. J. et al. (1984) Experiments with Gene Fusion, Cold Spring Harbor Laboratory Press). Oligonucleotides used as primers and probe were synthesized with the DNA synthesizer, Cyclone Plus (Milligene/Biosearch, Bedford, Mass.).

Construction and screening of the gene library SauIII AI-partially digested fragments of total DNA were ligated to the BamHI site in λEMBL3 arms according to Frischauf et al. (J. Mol. Biol. 170: 827-842 (1983)). The ligation mixture was packaged in vitro and transfected to E. coli P2392 according to the instructions of the suppliers (Stratagene, La Jolla, Calif.).

PCR amplification Primers for the chondroitinase ABC gene were designed according to the amino acid sequence of the chondroitinase ABC N-terminal region (SEQ ID NO:3) (FIG. 1-A). The primers were as follows 5'-GCNACNUCNAAYCCNGC-3' (P-1, sense)(SEQ ID NO:5);

5'-GCNACNAGYAAYCCNGC-3' (P-2, sense)(SEQ ID NO:6);

5'-UACGUYAGNCUYUADAU-3' (P-3, antisense)(SEQ ID NO:7);

5'-UACGUYUCRCUYUADAU-3' (P-4 antisense)(SEQ ID NO:8) (FIG. 1-A).

PCR was performed using a GeneAmp Kit (Takara Shuzo Co., Ltd., Japan) in a final volume of 100 μl which contained: 1 μg of genomic DNA solution, 10 μl of 10× PCR reaction buffer, 16 μl of 1.25 mM dNTP mixture, 0.6 nmol of mixed primers and 2.5 units of Taq DNA polymerase (Takara Shuzo Co., Ltd., Japan). The mixture was subjected to PCR amplification using the DNA thermal cycler (GeneAmp PCR System 9600, Perkin-Elmer/Cetus, Norwalk, Conn.) for 28 cycles. Each cycle was 1 minute at 93° C.(denaturation), 1.5 minutes at 50° C.(annealing) and 0.5 minute at 72° C.(elongation). PCR products were analyzed by electrophoresis through a 5% agarose gel (Nusieve GTG agarose, FMC Bioproducts, Rockford, Me.) and the 54 bp fragment encoding 17 amino acids of N-terminal region was cut out of the gel. Gel-purified PCR products were directly cloned into pT7 Blue PCR vector.

DNA Sequencing and Isolation of the Chondroitinase ABC Gene

Double-stranded plasmids purified by polyethylene glycol were denatured with alkali and sequenced by dideoxynucleotide chain termination method (Sanger, R. et al. (1977) Proc. Natl. Acad. Sci. USA 74: 5463-5467) using the sequence system, Hitachi WS10A Personal Sequencer (Hitachi Electronics Co., Ltd., Japan) Direct sequencing was done according to the method of Gyllesten & Erlich (Gyllensten, U. (1989) in PCR Technology, Erlich, H. A., Ed., Stockton Press, New York, pp. 45-60). PCR screening was carried out by the method of Olson et al.(Science 245: 1434-1435 (1989)). Plaque hybridization (Sambrook, J. et al. (1989) Molecular Cloning: A Laboratory Manual, 2nd ed., Cold Spring Harbor Laboratory Press) and Southern hybridization (Southern, E. M. (1975) J. Mol. Biol. 8: 503-517) were performed as outlined in the instructions of the supplier(Amersham Japan).

Primer extension analysis A 21-mer oligonucleotide(5'-CTA ATG GGT TAT TTT GTG CAA-3') (SEQ ID NO:4) complementary to the 5'-end (nucleotides 355-375) of the chondroitinase ABC gene was used as a primer. It was labeled with γ-$^{32}$P ATP (Amersham Japan) using polynucleotide kinase (Toyobo Co., Ltd., Japan). Total RNA of P. vulgaris was prepared according to the method of Aiba (J. Biol. Chem. 260: 3063-3070 (1985)). The labeled primer and 5 μg of total RNA were coprecipitated with ethanol. After annealing at 25° C. for 6 hours in a hybridization buffer (80% formamide, 40 mM PIPES(pH 6.4), 1 mM EDTA and 400 mM NaCl), 250 mM NaCl, 50 mM sodium acetate(pH 4.6), 4.5 mM $ZnSO_4$, 100 μg/ml heat-denatured salmon testes DNA and 15 unit/μl reverse transcriptase of Rous associated virus 2 (Takara Shuzo Co., Ltd., Japan) were added to the mixture. The primer extension reaction was carried out at 37° C. for 60 minutes.

Culture conditions Cells of E. coli XL1-Blue carrying recombinant plasmid were grown in 3 ml of LB broth(1% tryptone, 0.5% yeast extract, 1% NaCl, 25 μg/ml of chloramphenicol (pH 7.5)) at 37° C. for 16 hr with reciprocation (120 rpm, 5 cm stroke). The cells were harvested by centrifugation and washed twice with 0.85% saline solution. Cells were transferred to 100 ml of chondroitin 6-sulfate (Taiyo Fishery Co., Ltd., Japan) medium(0.7% $K_2HPO_4$, 0.3% $KH_2PO_4$, 0.01% $MgSO_4.7H_2O$, 0.1% $(NH_4)_2SO_4$, 0.1% yeast extract, 0.3% chondroitin 6-sulfate, 0.01% glucose, 25 μg/ml chloramphenicol (pH 7.5)) or glucose medium (composition is the same as that of chondroitin medium except that glucose (0.3%) was used as a carbon source) to make a final concentration of $A_{610}$=0.05. After incubation for 3 days at 37° C. with reciprocation, the cells were removed by centrifugation and degradation products of chondroitin 6-sulfate in the culture fluid were determined. The cells harvested from chondroitin and glucose media were washed twice with 50 mM Tris-HCl buffer (pH 8.0) and sonicated at 90 kHz for 5 minutes at 0° C. The cell debris were removed by centrifugation at 20,000 g for 30 minutes, and the supernatant was used for the assay of chondroitinase ABC.

Enzyme assay Chondroitinase ABC was assayed as described previously (Sato, N. et al. (1986) J. Ferment. Technol. 64: 155-159). The assay mixture (3 ml) containing 0.5% chondroitin 6-sulfate, 100 mM potassium phosphate buffer (pH 8.0) and cell extract, was incubated at 37° C. for 10 minutes, and the amount of N-acetylgalactosamine end group formed was determined by the method of Reissig (J. Biol. Chem. 217: 959-966 (1955)). Activity was expressed as the quantity of enzyme that catalyzed the formation of 1 μmol of unsaturated disaccharide (Δdi-6S) from chondroitin 6-sulfate per minute at 37° C.

Western blot analysis IgG specific to chondroitinase ABC was isolated from antisera raised in guinea pig using the technique described previously (Sato, N. et al. (1988) Biotechnol. Appl. Biochem. 10: 385-393). Proteins in crude cell extracts prepared from E. coli transformant were separated by sodium dodecyl sulfate-polyacrylamide gel electrophoresis (SDS-PAGE) as described previously (Sato, N. et al. (1986) Agric. Biol. Chem. 50: 1057-1059). Western blotting procedures were described previously (Sato, N. et al. (1989) Appl. Microbiol. Biotechnol. 30: 153-159).

EXAMPLE 1

Isolation and Sequence Determination of the Chondroitinase ABC Gene

According to the amino acid sequence of the N-terminal region of purified chondroitinase ABC (Ala-Thr-Ser-Asn-Pro-Ala-Phe-Asp-Pro-Lys-Asn-Leu-Met-Gln-Ser-Glu-Ile-Tyr (FIG. 1-A)(SEQ ID NO:3)), a set of degenerate oligo mixed primers (5'-GCNACNUCNAAYCCNGC-3' (P-1, sense)(SEQ ID NO:5); 5'-GCNACNAGYAAYCCNGC-3' (P-2, sense)(SEQ ID NO:6); 5'-UACGUY-AGNCUYUADAU-3' (P-3, antisense)(SEQ ID NO:7); 5'-UACGUYUCRCUYUADAU-3' (P-4 antisense)(SEQ ID NO:8))(FIG. 1-A) were synthesized as follows. To determine the appropriate primers for sequencing, PCR amplification of a combination of primers P-1(SEQ ID NO:5), P-2(SEQ ID NO:6) (sense) and P-3(SEQ ID NO:7), P-4(SEQ ID NO:8) (antisense) was performed. After agarose gel electrophoresis of these PCR products, a 54 bp fragment was extracted and directly inserted into pT7 Blue PCR vector, and the inserted fragment was sequenced. The nucleotide sequence of this fragment was found to be identical to the N-terminal amino acid sequence (FIG. 1-B) (SEQ ID NO:3). Then, using primer A (5'-GCAACCAGCAATCCTGCA-3')(SEQ ID NO:10), primer B ([5] *3'*-GACTACGTCAGGCTTT[T] *A*AAT-[3] *5'*) (SEQ ID NO:11) (FIG. 1-B) and 1 μg of P. vulgaris genomic DNA as a template, PCR analysis was performed and PCR products were analyzed by agarose gel electrophoresis. No non-specific PCR products were observed.

We then diluted γEMBL3 recombinant phage stock library. The diluted library was used for PCR screening. An unique 54 bp fragment was clearly detected until the dilution of $1/10^3$ ($2\times10^5$ pfu) phage stock solution as a template. The diluted phage solution was divided by $1/10(2\times10^4$ pfu) and was infected into E. coli P2392. They were then subjected to plaque hybridization using $^{32}$P-labeled probe (5'-CATTTGATCCTAAAAATCTGATGCA-3')(SEQ ID NO:9) (FIG. 1-B). The recombinant phages were chosen at random and analyzed by restriction mapping and Southern blotting. All phages contained common 4.2 kb EcoRV-EcoRI, 1.1 kb ClaI, and 2.0 kb EcoRV-HindIII fragments which hybridized strongly with the probe(SEQ ID NO:9). The restriction maps of three types of SalI fragments are shown in FIG. 1-C. Southern hybridization patterns of restricted genomic DNA from P. vulgaris matched the restriction map of these fragments. This result suggests that the 4.2 kb EcoRV-EcoRI fragment originated in the P. vulgaris genome, and therefore, the chondroitinase ABC gene exists as a single copy. When purified chondroitinase ABC from P. vulgaris was analyzed by SDS-PAGE, two types of chondroitinase ABC protein, one 100 kd protein and one subunit-like protein at 80 kd and 20 kd, were observed. The amino acid composition of the 100 kd protein and the subunit-like protein (80 kd and 20 kd) were quite similar, and the N-terminal amino acid sequences of the 100 kd and 20 kd proteins were identical. The results indicate that the two forms of chondroitinase ABC were not derived from two separate chondroitinase ABC genes.

The 5.2 kb SalI-EcoRI fragment in the recombinant γEMBL3 (No. 11-5) (FIG. 1-C) was subcloned into pSTV29 for sequencing and the resulting hybrid plasmid was designated pCHS6. The entire 3,063 bp nucleotide sequence of the coding region for the chondroitinase ABC gene as well as 224 and 200 nucleotides of the upstream and downstream regions, respectively, and the deduced amino acid sequence of chondroitinase ABC are shown in FIG. 7 (SEQ ID NO:1). The 25-mer oligonucleotide probe (SEQ ID NO:9) hybridized to nucleotide 314-337. The 16/18 nucleotide of primer A and the 17/18 nucleotide of primer B were the same in nucleotides 297-313 and 333-349. The G+C content of the chondroitinase ABC gene was 38.6%. The open reading frame encoded a polypeptide with a molecular weight of 115,218, which represents a precursor polypeptide containing a signal peptide sequence that is subsequently cleaved off at $Ala^{24}$-$Ala^{25}$ during secretion of the mature chondroitinase ABC protein having a molecular weight of 112,365.

EXAMPLE 2

Figure 3:
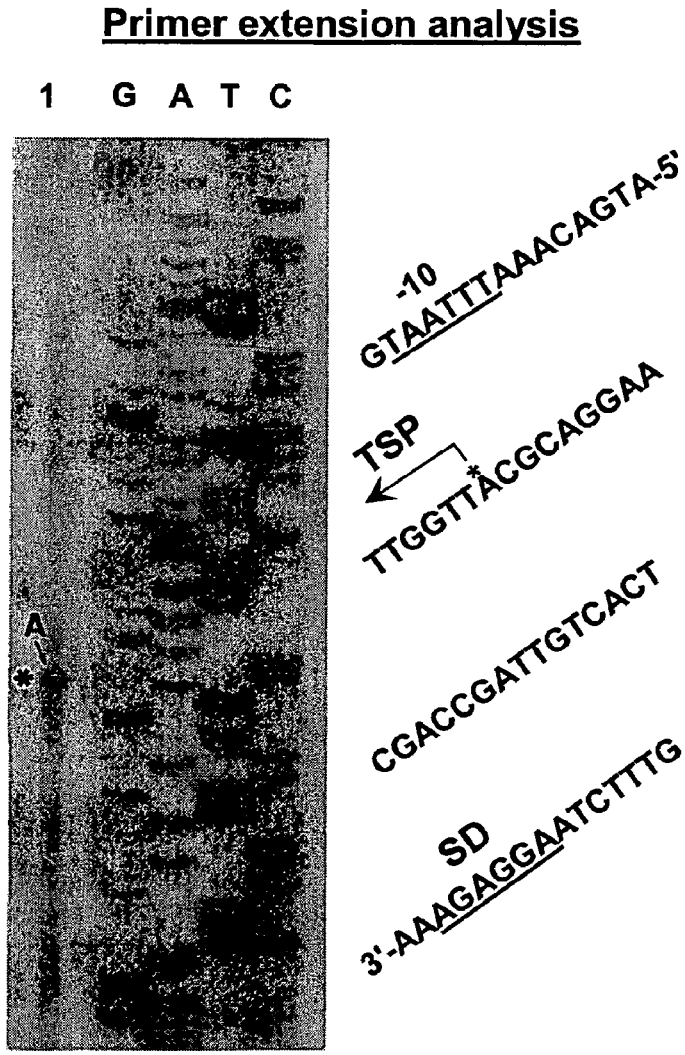
FIG. 3 shows primer extension analysis using a sequencing ladder (SEQ ID NO:15).

Analysis of the transcription region of the chondroitinase ABC gene In order to confirm the potential promoter region of the chondroitinase ABC gene, we amplified the region of nucleotide 112-283 using PCR. The PCR product was blunt-ended with T4 DNA polymerase and inserted into the SmaI site of the promoter selection vector, pMC 1871, and the hybrid plasmid, designated pCHSP, was introduced into E. coli JM109 (FIG. 2)(SEQ ID NO:14). The transformant was then cultured in an LB medium containing 25 μg/ml tetracycline at 37° C. for 14 hr, and β-galactosidase activity was assayed (Table I). Although the β-galactosidase activity of the E. coli transformant carrying pMC1871 was not detectable, the E. coli transformant carrying pCHSP produced β-galactosidase. This result indicates that the chondroitinase ABC gene can function as a promoter in E. coli cells. However, there is a possibility that the promoter recognized in E. coli cells may not be the promoter in P. vulgaris. To confirm that the promoter is recognized in P. vulgaris, primer extension analysis was carried out (FIG. 3) (SEQ ID NO:15). The transcription start point was localized to an adenosine 41 bp upstream from the start codon, ATG (FIG. 4) (SEQ ID NO:16). The potential pribnow box (TTTAAT) (nucleotides 169-174) was located 12 bp upstream from the transcription start point (FIG. 4) (SEQ ID NO: 16). However, the −35 consensus sequence was not found near 35 bp upstream of the start point except for 47 bp upstream of the start point (TAGGCA) (FIG. 4) (SEQ ID NO:16). The Shine-Dalgarno ribosomal binding site (AGGAGA) (nucleotides 213-218) was found 9 bp upstream from the initiation codon, ATG (FIG. 4) (SEQ ID NO: 16). A terminator-like palindrome sequence consisting of an 11 nucleotide stem with a 4 nucleotide loop structure (stacking energy 24 kcal/mol) was located 9 nucleotides downstream from the stop codon, TGA (FIG. 4) (SEQ ID NO:16). Judging from the secondary structure prediction, this stem-loop structure resembles a σ-dependent transcription terminator.

TABLE I

β-Galactosidase productivity of *E-coli* transformants

| Strain *E. coli* JM109 | β-Galactosidase activity Activity (U/mi-culture) | Specific activity/ (U/mg-protein) |
|---|---|---|
| /pMC1871 | 0 | 0 |
| /pCHSP | 0.2 | 0.4 |

1 U is defined as the amount that produced 1 μmol of α-nitrophenol per h.

EXAMPLE 3

Figure 5:
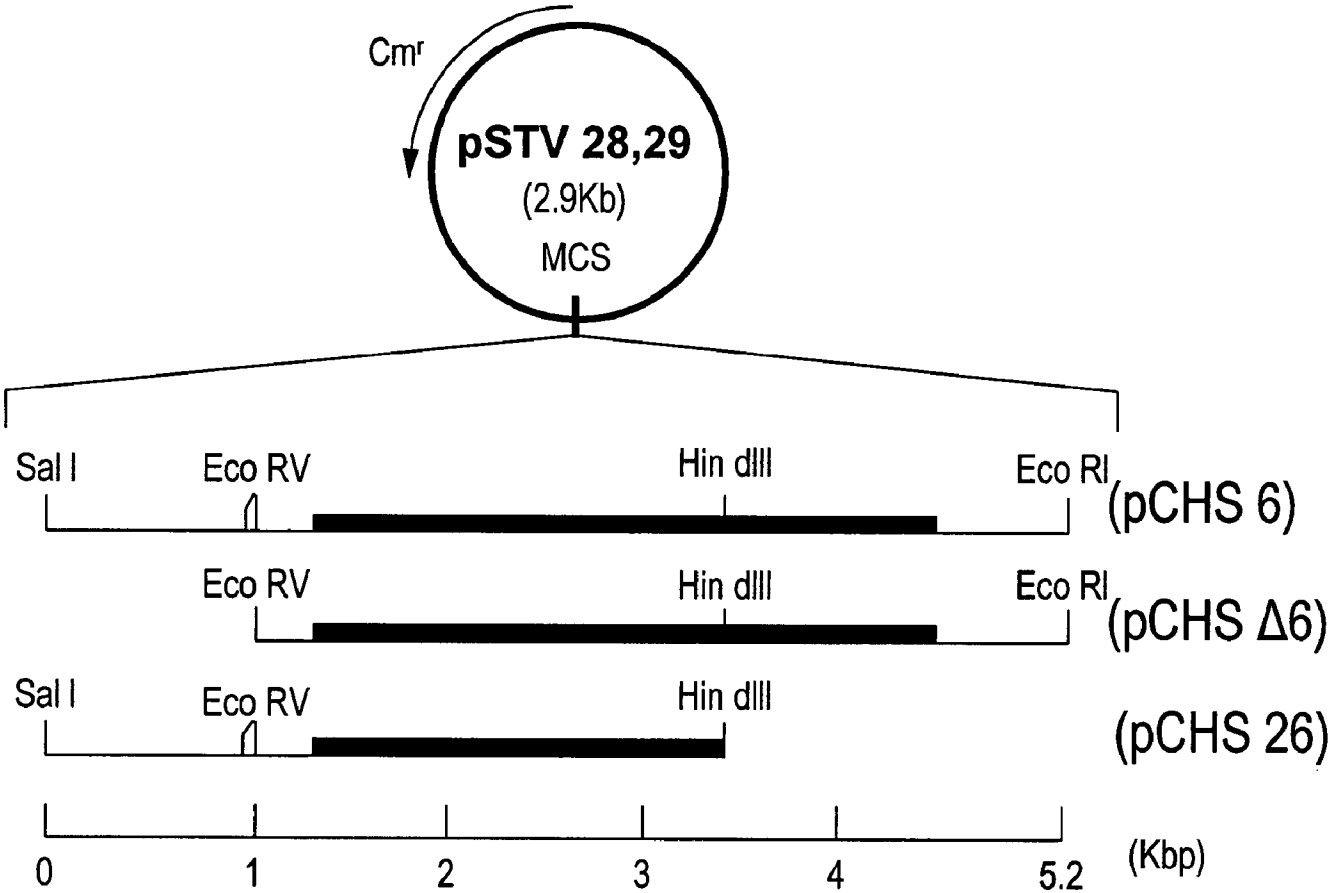
FIG. 5 shows the construction of plasmids pCHS 6, pCHSΔ 6, and pCHS 26 each of which contains a fragment of the chondroitinase ABC gene.

Production of chondroitinase ABC from E. coli transformant To demonstrate that the isolated gene codes for chondroitinase ABC, we constructed pCHSΔ6 and pCHS26 (FIG. 5). pCHSΔ6 was constructed by removing the SalI-EcoRV region (about 1 kb) upstream from the promoter region from the chondroitinase ABC gene. While pCHS26 was constructed by removing the HindIII-EcoRI region which corresponded to about one third of the 3'-terminal region of the chondroitinase ABC structural gene. These plasmids (pCHS6, pCHSΔ6 and pCHS26) were introduced into E. coli XL 1-Blue, and E. coli transformants were cultured in chondroitin or glucose medium, and chondroitinase ABC activities were assayed using the crude extract. The culture fluids of the chondroitin medium were also analyzed to determine degradation products of chondroitin 6-sulfate (Table II). The E. coli transformant carrying pCHS6 (containing a 1.0 kb fragment upstream from the promoter) produced the chondroitinase ABC when cultured in chondroitin medium, however, no chondroitinase ABC activity was observed when the transformant was cultured in glucose medium. In contrast, the E. coli transformant carrying pCHSΔ6 produced chondroitinase ABC when cultured in either chondroitin or glucose media. The production levels of chondroitinase ABC, cultured in chondroitin media, were 2.6 fold(/pCHS6) and 187 fold(/pCHSΔ6) higher than that of P. vulgaris. Even cultured in glucose medium, the production level of chondroitinase ABC in the E. coli transformant carrying pCHSΔ6 was 187 fold higher than that of P. vulgaris cultured in chondroitin medium. This result suggests that the regulatory sequence might be in the SalI-EcoRV region. Although chondroitin 6-sulfate added to the medium was degraded (p/CHS6 and /pCHSΔ6), E. coli transformants were not able to utilize chondroitin sulfate as a carbon source.

TABLE II

Chondroitinase ABC Activity of *E. coli* Transformants

| Strain | Intracellular chondroitinase ABC activity: Chondroitin medium (0.3%) Activity[a] | Chondroitin medium (0.3%) Specific[b] activity | Glucose medium (0.3%) Actiity | Glucose medium (0.3%) Specific activity | Cultured medium Amount of 4,5Δ chondroitin-6 (μg/ml-culture) |
|---|---|---|---|---|---|
| *E. coli* XL1-Blue | 0 | 0 | 0 | 0 | 0 |
| /pSTV29 | 0 | 0 | 0 | 0 | 0 |
| /pCHS6 | $4.1 \times 10^{-3}$ | $1.6 \times 10^{-2}$ | 0 | 0 | 192.7 |
| /pCHS26 | 0 | 0 | 0 | 0 | 0 |
| /pCHSΔ6 | 0.3 | 1.2 | 0.3 | 0.5 | 1542.4 |
| *P. vulgaris* | $1.6 \times 10^{-3}$ | $1.2 \times 10^{-2}$ | 0 | 0 | 1738.4 |

[a]1 U: enzyme activity producing 1 μmol, 4,5Δ chondroitin-6 per min
[b]U/mg-protein It has been reported that the Bacteriodes thetaiotaomicron chondroitin lyase II gene is adjacent to the chondrosulfatase gene which may be a part of an operon (Guthrie, E. P. et al. (1987) J. Bacteriol. 169: 1192-1199). These same investigators reported that the promoter for this gene recognized in E. coli may not be the promoter from which the chondroitin lyase II gene is transcribed from in B. thetaiotaomicron (Ld.) In fact, a putative open reading frame 12 bp upstream from the initiation codon, ATG, was found in the chondroitinase ABC gene (FIG. 4) (SEQ ID NO: 16). However, primer extension analysis revealed that the transcription start point is located 41 bp upstream from the initiation codon in P. vulgaris(FIG. 3) (SEQ ID NO: 15). Even though the chondroitinase ABC gene from P. vulgaris cells was also part of an operon, chondroitinase ABC gene was transcribed 41 bp upstream from the initiation codon in P. vulgaris cells.

The secondary structure of chondroitinase ABC was estimated by the method of Chou and Fasman (Annu. Rev. Biochem. 47: 251-276 (1978)). A highly complex region was found between amino acid residues 450 and 850. The pCHS26 lacks one-third of the chondroitinase ABC gene encoding the C-terminal region (amino acid residues 646-1021). Removing this region of the enzyme caused the disappearance of chondroitinase ABC activity (Table II). This result suggests that there might be an active site in this region.

Figure 6:
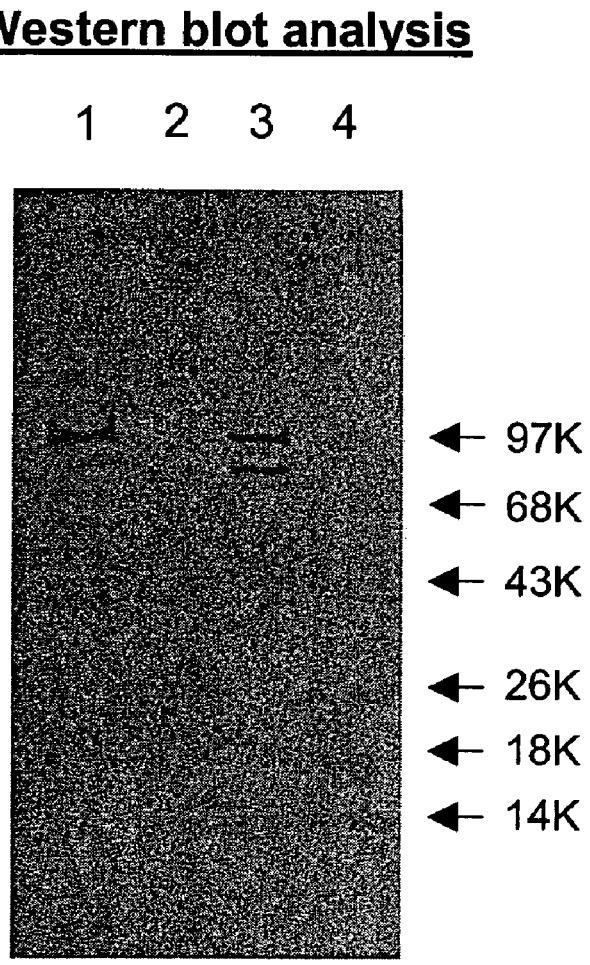
FIG. 6 shows SDS-PAGE and immunoblot analysis of recombinant chondroitinase ABC protein produced by pCHSΔ 6 transformed E. coli (lane 1); protein produced by pSTV 29 without the chondroitinase ABC gene in E. coli (lane 2); natural chondroitinase ABC produced by P. vulgaris (lane 3); and molecular weight markers (lane 4).

Recombinant chondroitinase ABC produced by E. coli carrying pCHSΔ6 was analyzed by SDS-PAGE followed by immunoblotting (FIG. 6). The immunoblotting patterns of recombinant and native chondroitinase ABC (100 kd) were quite similar. Our previous report showed chondroitinase ABC purified from P. vulgaris was a subunit structure consisting of a 90 kd and a 20 kd protein by SDS-PAGE (Sato, N.

et al. (1986) Agric. Biol. Chem. 50: 1057-1059), because this subunit protein would not be separated even using gel filtration and other chromatographic techniques. However, by analysis of the N-terminal sequence, we found that the 100 kd protein and the 20 kd protein had the same N-terminal amino acid sequence. By immunoblot analysis, the 80 kd protein also reacts with IgG specific to the 100 kd protein. Furthermore, genomic restriction analysis suggested that chondroitinase ABC gene was a single gene. When we extracted the 100 kd band of chondroitinase ABC from the acrylamide gel and electrophoresed it again in SDS-PAGE, 80 kd and 20 kd bands appeared. The purified chondroitinase ABC contained no protease activity. These results suggest that chondroitinase ABC was partially digested not enzymatically, but physically in the course of sample preparation for SDS-PAGE.

Equivalents

Those skilled in the art will recognize, or be able to ascertain using no more than routine experimentation, numerous equivalents to the specific procedures described herein. Such equivalents are considered to be within the scope of this invention and are covered by the following claims.

SEQUENCE LISTING

```
<160> NUMBER OF SEQ ID NOS: 17

<210> SEQ ID NO 1
<211> LENGTH: 3066
<212> TYPE: DNA
<213> ORGANISM: Proteus vulgaris
<220> FEATURE:
<221> NAME/KEY: CDS
<222> LOCATION: (1)..(3063)

<400> SEQUENCE: 1

atg ccg ata ttt cgt ttt act gca ctt gca atg aca ttg ggg cta tta       48
Met Pro Ile Phe Arg Phe Thr Ala Leu Ala Met Thr Leu Gly Leu Leu
1               5                   10                  15

tca gcg cct tat aac gcg atg gca gcc acc agc aat cct gca ttt gat       96
Ser Ala Pro Tyr Asn Ala Met Ala Ala Thr Ser Asn Pro Ala Phe Asp
            20                  25                  30

cct aaa aat ctg atg cag tca gaa att tac cat ttt gca caa aat aac      144
Pro Lys Asn Leu Met Gln Ser Glu Ile Tyr His Phe Ala Gln Asn Asn
        35                  40                  45

cca tta gca gac ttc tca tca gat aaa aac tca ata cta acg tta tct      192
Pro Leu Ala Asp Phe Ser Ser Asp Lys Asn Ser Ile Leu Thr Leu Ser
    50                  55                  60

gat aaa cgt agc att atg gga aac caa tct ctt tta tgg aaa tgg aaa      240
Asp Lys Arg Ser Ile Met Gly Asn Gln Ser Leu Leu Trp Lys Trp Lys
65                  70                  75                  80

ggt ggt agt agc ttt act tta cat aaa aaa ctg att gtc ccc acc gat      288
Gly Gly Ser Ser Phe Thr Leu His Lys Lys Leu Ile Val Pro Thr Asp
                85                  90                  95

aaa gaa gca tct aaa gca tgg gga cgc tca tct acc ccc gtt ttc tca      336
Lys Glu Ala Ser Lys Ala Trp Gly Arg Ser Ser Thr Pro Val Phe Ser
            100                 105                 110

ttt tgg ctt tac aat gaa aaa ccg att gat ggt tat ctt act atc gat      384
Phe Trp Leu Tyr Asn Glu Lys Pro Ile Asp Gly Tyr Leu Thr Ile Asp
        115                 120                 125

ttc gga gaa aaa ctc att tca acc agt gag gct cag gca ggc ttt aaa      432
Phe Gly Glu Lys Leu Ile Ser Thr Ser Glu Ala Gln Ala Gly Phe Lys
    130                 135                 140

gta aaa tta gat ttc act ggc tgg cgt gct gtg gga gtc tct tta aat      480
Val Lys Leu Asp Phe Thr Gly Trp Arg Ala Val Gly Val Ser Leu Asn
145                 150                 155                 160

aac gat ctt gaa aat cga gag atg acc tta aat gca acc aat acc tcc      528
Asn Asp Leu Glu Asn Arg Glu Met Thr Leu Asn Ala Thr Asn Thr Ser
                165                 170                 175

tct gat ggt act caa gac agc att ggg cgt tct tta ggt gct aaa gtc      576
Ser Asp Gly Thr Gln Asp Ser Ile Gly Arg Ser Leu Gly Ala Lys Val
            180                 185                 190

gat agt att cgt ttt aaa gcg cct tct aat gtg agt cag ggt gaa atc      624
Asp Ser Ile Arg Phe Lys Ala Pro Ser Asn Val Ser Gln Gly Glu Ile
        195                 200                 205
```

```
tat atc gac cgt att atg ttt tct gtc gat gat gct cgc tac caa tgg      672
Tyr Ile Asp Arg Ile Met Phe Ser Val Asp Asp Ala Arg Tyr Gln Trp
    210                 215                 220

tct gat tat caa gta aaa act cgc tta tca gaa cct gaa att caa ttt      720
Ser Asp Tyr Gln Val Lys Thr Arg Leu Ser Glu Pro Glu Ile Gln Phe
225                 230                 235                 240

cac aac gta aag cca caa cta cct gta aca cct gaa aat tta gcg gcc      768
His Asn Val Lys Pro Gln Leu Pro Val Thr Pro Glu Asn Leu Ala Ala
                245                 250                 255

att gat ctt att cgc caa cgt cta att aat gaa ttt gtc gga ggt gaa      816
Ile Asp Leu Ile Arg Gln Arg Leu Ile Asn Glu Phe Val Gly Gly Glu
            260                 265                 270

aaa gag aca aac ctc gca tta gaa gag aat atc agc aaa tta aaa agt      864
Lys Glu Thr Asn Leu Ala Leu Glu Glu Asn Ile Ser Lys Leu Lys Ser
        275                 280                 285

gat ttc gat gct ctt aat att cac act tta gca aat ggt gga acg caa      912
Asp Phe Asp Ala Leu Asn Ile His Thr Leu Ala Asn Gly Gly Thr Gln
    290                 295                 300

ggc aga cat ctg atc act gat aaa caa atc att att tat caa cca gag      960
Gly Arg His Leu Ile Thr Asp Lys Gln Ile Ile Ile Tyr Gln Pro Glu
305                 310                 315                 320

aat ctt aac tcc caa gat aaa caa cta ttt gat aat tat gtt att tta     1008
Asn Leu Asn Ser Gln Asp Lys Gln Leu Phe Asp Asn Tyr Val Ile Leu
                325                 330                 335

ggt aat tac acg aca tta atg ttt aat att agc cgt gct tat gtg ctg     1056
Gly Asn Tyr Thr Thr Leu Met Phe Asn Ile Ser Arg Ala Tyr Val Leu
            340                 345                 350

gaa aaa gat ccc aca caa aag gcg caa cta aag cag atg tac tta tta     1104
Glu Lys Asp Pro Thr Gln Lys Ala Gln Leu Lys Gln Met Tyr Leu Leu
        355                 360                 365

atg aca aag cat tta tta gat caa ggc ttt gtt aaa ggg agt gct tta     1152
Met Thr Lys His Leu Leu Asp Gln Gly Phe Val Lys Gly Ser Ala Leu
    370                 375                 380

gtg aca acc cat cac tgg gga tac agt tct cgt tgg tgg tat att tcc     1200
Val Thr Thr His His Trp Gly Tyr Ser Ser Arg Trp Trp Tyr Ile Ser
385                 390                 395                 400

acg tta tta atg tct gat gca cta aaa gaa gcg aac cta caa act caa     1248
Thr Leu Leu Met Ser Asp Ala Leu Lys Glu Ala Asn Leu Gln Thr Gln
                405                 410                 415

gtt tat gat tca tta ctg tgg tat tca cgt gag ttt aaa agt agt ttt     1296
Val Tyr Asp Ser Leu Leu Trp Tyr Ser Arg Glu Phe Lys Ser Ser Phe
            420                 425                 430

gat atg aaa gta agt gct gat agc tct gat cta gat tat ttc aat acc     1344
Asp Met Lys Val Ser Ala Asp Ser Ser Asp Leu Asp Tyr Phe Asn Thr
        435                 440                 445

tta tct cgc caa cat tta gcc tta tta tta cta gag cct gat gat caa     1392
Leu Ser Arg Gln His Leu Ala Leu Leu Leu Leu Glu Pro Asp Asp Gln
    450                 455                 460

aag cgt atc aac tta gtt aat act ttc agc cat tat atc act ggc gca     1440
Lys Arg Ile Asn Leu Val Asn Thr Phe Ser His Tyr Ile Thr Gly Ala
465                 470                 475                 480

tta acg caa gtg cca ccg ggt ggt aaa gat ggt tta cgc cct gat ggt     1488
Leu Thr Gln Val Pro Pro Gly Gly Lys Asp Gly Leu Arg Pro Asp Gly
                485                 490                 495

aca gca tgg cga cat gaa ggc aac tat ccg ggc tac tct ttc cca gcc     1536
Thr Ala Trp Arg His Glu Gly Asn Tyr Pro Gly Tyr Ser Phe Pro Ala
            500                 505                 510

ttt aaa aat gcc tct cag ctt att tat tta tta cgc gat aca cca ttt     1584
Phe Lys Asn Ala Ser Gln Leu Ile Tyr Leu Leu Arg Asp Thr Pro Phe
        515                 520                 525
```

```
tca gtg ggt gaa agt ggt tgg aat aac ctg aaa aaa gcg atg gtt tca     1632
Ser Val Gly Glu Ser Gly Trp Asn Asn Leu Lys Lys Ala Met Val Ser
    530                 535                 540

gcg tgg atc tac agt aat cca gaa gtt gga tta ccg ctt gca gga aga     1680
Ala Trp Ile Tyr Ser Asn Pro Glu Val Gly Leu Pro Leu Ala Gly Arg
545                 550                 555                 560

cac cct ttt aac tca cct tcg tta aaa tca gtc gct caa ggc tat tac     1728
His Pro Phe Asn Ser Pro Ser Leu Lys Ser Val Ala Gln Gly Tyr Tyr
                565                 570                 575

tgg ctt gcc atg tct gca aaa tca tcg cct gat aaa aca ctt gca tct     1776
Trp Leu Ala Met Ser Ala Lys Ser Ser Pro Asp Lys Thr Leu Ala Ser
            580                 585                 590

att tat ctt gcg att agt gat aaa aca caa aat gaa tca act gct att     1824
Ile Tyr Leu Ala Ile Ser Asp Lys Thr Gln Asn Glu Ser Thr Ala Ile
        595                 600                 605

ttt gga gaa act att aca cca gcg tct tta cct caa ggt ttc tat gcc     1872
Phe Gly Glu Thr Ile Thr Pro Ala Ser Leu Pro Gln Gly Phe Tyr Ala
    610                 615                 620

ttt aat ggc ggt gct ttt ggt att cat cgt tgg caa gat aaa atg gtg     1920
Phe Asn Gly Gly Ala Phe Gly Ile His Arg Trp Gln Asp Lys Met Val
625                 630                 635                 640

aca ctg aaa gct tat aac acc aat gtt tgg tca tct gaa att tat aac     1968
Thr Leu Lys Ala Tyr Asn Thr Asn Val Trp Ser Ser Glu Ile Tyr Asn
                645                 650                 655

aaa gat aac cgt tat ggc cgt tac caa agt cat ggt gtc gct caa ata     2016
Lys Asp Asn Arg Tyr Gly Arg Tyr Gln Ser His Gly Val Ala Gln Ile
            660                 665                 670

gtg agt aat ggc tcg cag ctt tca cag ggc tat cag caa gaa ggt tgg     2064
Val Ser Asn Gly Ser Gln Leu Ser Gln Gly Tyr Gln Gln Glu Gly Trp
        675                 680                 685

gat tgg aat aga atg caa ggg gca acc act att cac ctt cct ctt aaa     2112
Asp Trp Asn Arg Met Gln Gly Ala Thr Thr Ile His Leu Pro Leu Lys
    690                 695                 700

gac tta gac agt cct aaa cct cat acc tta atg caa cgt gga gag cgt     2160
Asp Leu Asp Ser Pro Lys Pro His Thr Leu Met Gln Arg Gly Glu Arg
705                 710                 715                 720

gga ttt agc gga aca tca tcc ctt gaa ggt caa tat ggc atg atg gca     2208
Gly Phe Ser Gly Thr Ser Ser Leu Glu Gly Gln Tyr Gly Met Met Ala
                725                 730                 735

ttc gat ctt att tat ccc gcc aat ctt gag cgt ttt gat cct aat ttc     2256
Phe Asp Leu Ile Tyr Pro Ala Asn Leu Glu Arg Phe Asp Pro Asn Phe
            740                 745                 750

act gcg aaa aag agt gta tta gcc gct gat aat cac tta att ttt att     2304
Thr Ala Lys Lys Ser Val Leu Ala Ala Asp Asn His Leu Ile Phe Ile
        755                 760                 765

ggt agc aat ata aat agt agt gat aaa aat aaa aat gtt gaa acg acc     2352
Gly Ser Asn Ile Asn Ser Ser Asp Lys Asn Lys Asn Val Glu Thr Thr
    770                 775                 780

tta ttc caa cat gcc att act cca aca tta aat acc ctt tgg att aat     2400
Leu Phe Gln His Ala Ile Thr Pro Thr Leu Asn Thr Leu Trp Ile Asn
785                 790                 795                 800

gga caa aag ata gaa aac atg cct tat caa aca aca ctt caa caa ggt     2448
Gly Gln Lys Ile Glu Asn Met Pro Tyr Gln Thr Thr Leu Gln Gln Gly
                805                 810                 815

gat tgg tta att gat agc aat ggc aat ggt tac tta att act caa gca     2496
Asp Trp Leu Ile Asp Ser Asn Gly Asn Gly Tyr Leu Ile Thr Gln Ala
            820                 825                 830

gaa aaa gta aat gta agt cgc caa cat cag gtt tca gcg gaa aat aaa     2544
Glu Lys Val Asn Val Ser Arg Gln His Gln Val Ser Ala Glu Asn Lys
        835                 840                 845
```

```
aat cgc caa ccg aca gaa gga aac ttt agc tcg gca tgg atc gat cac     2592
Asn Arg Gln Pro Thr Glu Gly Asn Phe Ser Ser Ala Trp Ile Asp His
    850                 855                 860

agc act cgc ccc aaa gat gcc agt tat gag tat atg gtc ttt tta gat     2640
Ser Thr Arg Pro Lys Asp Ala Ser Tyr Glu Tyr Met Val Phe Leu Asp
865                 870                 875                 880

gcg aca cct gaa aaa atg gga gag atg gca caa aaa ttc cgt gaa aat     2688
Ala Thr Pro Glu Lys Met Gly Glu Met Ala Gln Lys Phe Arg Glu Asn
                885                 890                 895

aat ggg tta tat cag gtt ctt cgt aag gat aaa gac gtt cat att att     2736
Asn Gly Leu Tyr Gln Val Leu Arg Lys Asp Lys Asp Val His Ile Ile
            900                 905                 910

ctc gat aaa ctc agc aat gta acg gga tat gcc ttt tat cag cca gca     2784
Leu Asp Lys Leu Ser Asn Val Thr Gly Tyr Ala Phe Tyr Gln Pro Ala
        915                 920                 925

tca att gaa gac aaa tgg atc aaa aag gtt aat aaa cct gca att gtg     2832
Ser Ile Glu Asp Lys Trp Ile Lys Lys Val Asn Lys Pro Ala Ile Val
    930                 935                 940

atg act cat cga caa aaa gac act ctt att gtc agt gca gtt aca cct     2880
Met Thr His Arg Gln Lys Asp Thr Leu Ile Val Ser Ala Val Thr Pro
945                 950                 955                 960

gat tta aat atg act cgc caa aaa gca gca act cct gtc acc atc aat     2928
Asp Leu Asn Met Thr Arg Gln Lys Ala Ala Thr Pro Val Thr Ile Asn
                965                 970                 975

gtc acg att aat ggc aaa tgg caa tct gct gat aaa aat agt gaa gtg     2976
Val Thr Ile Asn Gly Lys Trp Gln Ser Ala Asp Lys Asn Ser Glu Val
            980                 985                 990

aaa tat cag gtt tct ggt gat aac  act gaa ctg acg ttt  acg agt tac   3024
Lys Tyr Gln Val Ser Gly Asp Asn  Thr Glu Leu Thr Phe  Thr Ser Tyr
        995                 1000                1005

ttt ggt  att cca caa gaa atc  aaa ctc tcg cca ctc  cct tga          3066
Phe Gly  Ile Pro Gln Glu Ile  Lys Leu Ser Pro Leu  Pro
    1010                1015                1020


<210> SEQ ID NO 2
<211> LENGTH: 1021
<212> TYPE: PRT
<213> ORGANISM: Proteus vulgaris

<400> SEQUENCE: 2

Met Pro Ile Phe Arg Phe Thr Ala Leu Ala Met Thr Leu Gly Leu Leu
1               5                   10                  15

Ser Ala Pro Tyr Asn Ala Met Ala Ala Thr Ser Asn Pro Ala Phe Asp
            20                  25                  30

Pro Lys Asn Leu Met Gln Ser Glu Ile Tyr His Phe Ala Gln Asn Asn
        35                  40                  45

Pro Leu Ala Asp Phe Ser Ser Asp Lys Asn Ser Ile Leu Thr Leu Ser
    50                  55                  60

Asp Lys Arg Ser Ile Met Gly Asn Gln Ser Leu Leu Trp Lys Trp Lys
65                  70                  75                  80

Gly Gly Ser Ser Phe Thr Leu His Lys Lys Leu Ile Val Pro Thr Asp
                85                  90                  95

Lys Glu Ala Ser Lys Ala Trp Gly Arg Ser Ser Thr Pro Val Phe Ser
            100                 105                 110

Phe Trp Leu Tyr Asn Glu Lys Pro Ile Asp Gly Tyr Leu Thr Ile Asp
        115                 120                 125

Phe Gly Glu Lys Leu Ile Ser Thr Ser Glu Ala Gln Ala Gly Phe Lys
    130                 135                 140
```

```
Val Lys Leu Asp Phe Thr Gly Trp Arg Ala Val Gly Val Ser Leu Asn
145                 150                 155                 160

Asn Asp Leu Glu Asn Arg Glu Met Thr Leu Asn Ala Thr Asn Thr Ser
                165                 170                 175

Ser Asp Gly Thr Gln Asp Ser Ile Gly Arg Ser Leu Gly Ala Lys Val
            180                 185                 190

Asp Ser Ile Arg Phe Lys Ala Pro Ser Asn Val Ser Gln Gly Glu Ile
        195                 200                 205

Tyr Ile Asp Arg Ile Met Phe Ser Val Asp Asp Ala Arg Tyr Gln Trp
    210                 215                 220

Ser Asp Tyr Gln Val Lys Thr Arg Leu Ser Glu Pro Glu Ile Gln Phe
225                 230                 235                 240

His Asn Val Lys Pro Gln Leu Pro Val Thr Pro Glu Asn Leu Ala Ala
                245                 250                 255

Ile Asp Leu Ile Arg Gln Arg Leu Ile Asn Glu Phe Val Gly Gly Glu
            260                 265                 270

Lys Glu Thr Asn Leu Ala Leu Glu Glu Asn Ile Ser Lys Leu Lys Ser
        275                 280                 285

Asp Phe Asp Ala Leu Asn Ile His Thr Leu Ala Asn Gly Gly Thr Gln
    290                 295                 300

Gly Arg His Leu Ile Thr Asp Lys Gln Ile Ile Ile Tyr Gln Pro Glu
305                 310                 315                 320

Asn Leu Asn Ser Gln Asp Lys Gln Leu Phe Asp Asn Tyr Val Ile Leu
                325                 330                 335

Gly Asn Tyr Thr Thr Leu Met Phe Asn Ile Ser Arg Ala Tyr Val Leu
            340                 345                 350

Glu Lys Asp Pro Thr Gln Lys Ala Gln Leu Lys Gln Met Tyr Leu Leu
        355                 360                 365

Met Thr Lys His Leu Leu Asp Gln Gly Phe Val Lys Gly Ser Ala Leu
    370                 375                 380

Val Thr Thr His His Trp Gly Tyr Ser Ser Arg Trp Trp Tyr Ile Ser
385                 390                 395                 400

Thr Leu Leu Met Ser Asp Ala Leu Lys Glu Ala Asn Leu Gln Thr Gln
                405                 410                 415

Val Tyr Asp Ser Leu Leu Trp Tyr Ser Arg Glu Phe Lys Ser Ser Phe
            420                 425                 430

Asp Met Lys Val Ser Ala Asp Ser Ser Asp Leu Asp Tyr Phe Asn Thr
        435                 440                 445

Leu Ser Arg Gln His Leu Ala Leu Leu Leu Leu Glu Pro Asp Asp Gln
    450                 455                 460

Lys Arg Ile Asn Leu Val Asn Thr Phe Ser His Tyr Ile Thr Gly Ala
465                 470                 475                 480

Leu Thr Gln Val Pro Pro Gly Gly Lys Asp Gly Leu Arg Pro Asp Gly
                485                 490                 495

Thr Ala Trp Arg His Glu Gly Asn Tyr Pro Gly Tyr Ser Phe Pro Ala
            500                 505                 510

Phe Lys Asn Ala Ser Gln Leu Ile Tyr Leu Leu Arg Asp Thr Pro Phe
        515                 520                 525

Ser Val Gly Glu Ser Gly Trp Asn Asn Leu Lys Lys Ala Met Val Ser
    530                 535                 540

Ala Trp Ile Tyr Ser Asn Pro Glu Val Gly Leu Pro Leu Ala Gly Arg
545                 550                 555                 560

His Pro Phe Asn Ser Pro Ser Leu Lys Ser Val Ala Gln Gly Tyr Tyr
                565                 570                 575
```

```
Trp Leu Ala Met Ser Ala Lys Ser Ser Pro Asp Lys Thr Leu Ala Ser
            580                 585                 590

Ile Tyr Leu Ala Ile Ser Asp Lys Thr Gln Asn Glu Ser Thr Ala Ile
        595                 600                 605

Phe Gly Glu Thr Ile Thr Pro Ala Ser Leu Pro Gln Gly Phe Tyr Ala
    610                 615                 620

Phe Asn Gly Gly Ala Phe Gly Ile His Arg Trp Gln Asp Lys Met Val
625                 630                 635                 640

Thr Leu Lys Ala Tyr Asn Thr Asn Val Trp Ser Ser Glu Ile Tyr Asn
                645                 650                 655

Lys Asp Asn Arg Tyr Gly Arg Tyr Gln Ser His Gly Val Ala Gln Ile
            660                 665                 670

Val Ser Asn Gly Ser Gln Leu Ser Gln Gly Tyr Gln Gln Glu Gly Trp
        675                 680                 685

Asp Trp Asn Arg Met Gln Gly Ala Thr Thr Ile His Leu Pro Leu Lys
    690                 695                 700

Asp Leu Asp Ser Pro Lys Pro His Thr Leu Met Gln Arg Gly Glu Arg
705                 710                 715                 720

Gly Phe Ser Gly Thr Ser Ser Leu Glu Gly Gln Tyr Gly Met Met Ala
                725                 730                 735

Phe Asp Leu Ile Tyr Pro Ala Asn Leu Glu Arg Phe Asp Pro Asn Phe
            740                 745                 750

Thr Ala Lys Lys Ser Val Leu Ala Ala Asp Asn His Leu Ile Phe Ile
        755                 760                 765

Gly Ser Asn Ile Asn Ser Ser Asp Lys Asn Lys Asn Val Glu Thr Thr
    770                 775                 780

Leu Phe Gln His Ala Ile Thr Pro Thr Leu Asn Thr Leu Trp Ile Asn
785                 790                 795                 800

Gly Gln Lys Ile Glu Asn Met Pro Tyr Gln Thr Thr Leu Gln Gln Gly
                805                 810                 815

Asp Trp Leu Ile Asp Ser Asn Gly Asn Gly Tyr Leu Ile Thr Gln Ala
            820                 825                 830

Glu Lys Val Asn Val Ser Arg Gln His Gln Val Ser Ala Glu Asn Lys
        835                 840                 845

Asn Arg Gln Pro Thr Glu Gly Asn Phe Ser Ser Ala Trp Ile Asp His
    850                 855                 860

Ser Thr Arg Pro Lys Asp Ala Ser Tyr Glu Tyr Met Val Phe Leu Asp
865                 870                 875                 880

Ala Thr Pro Glu Lys Met Gly Glu Met Ala Gln Lys Phe Arg Glu Asn
                885                 890                 895

Asn Gly Leu Tyr Gln Val Leu Arg Lys Asp Lys Asp Val His Ile Ile
            900                 905                 910

Leu Asp Lys Leu Ser Asn Val Thr Gly Tyr Ala Phe Tyr Gln Pro Ala
        915                 920                 925

Ser Ile Glu Asp Lys Trp Ile Lys Lys Val Asn Lys Pro Ala Ile Val
    930                 935                 940

Met Thr His Arg Gln Lys Asp Thr Leu Ile Val Ser Ala Val Thr Pro
945                 950                 955                 960

Asp Leu Asn Met Thr Arg Gln Lys Ala Ala Thr Pro Val Thr Ile Asn
                965                 970                 975

Val Thr Ile Asn Gly Lys Trp Gln Ser Ala Asp Lys Asn Ser Glu Val
            980                 985                 990

Lys Tyr Gln Val Ser Gly Asp Asn  Thr Glu Leu Thr Phe  Thr Ser Tyr
```

995 1000 1005

Phe Gly Ile Pro Gln Glu Ile Lys Leu Ser Pro Leu Pro
1010 1015 1020

<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 3

Ala Thr Ser Asn Pro Ala Phe Asp Pro Lys Asn Leu Met Gln Ser Glu
1 5 10 15

Ile Tyr

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 4 ctaatgggtt attttgtgca a 21

<210> SEQ ID NO 5
<211> LENGTH: 17
<212> TYPE: RNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (3)..(3)
<223> OTHER INFORMATION: a, c, u or g
<220> FEATURE:
<221> NAME/KEY: modified_base
<222> LOCATION: (6)..(6)
<223> OTHER INFORMATION: a, c, u or g
<220> FEATURE:
<221> NAME/KEY: modified_base
<222> LOCATION: (9)..(9)
<223> OTHER INFORMATION: a, c, u or g
<220> FEATURE:
<221> NAME/KEY: modified_base
<222> LOCATION: (15)..(15)
<223> OTHER INFORMATION: a, c, u or g

<400> SEQUENCE: 5 gcnacnucna ayccngc 17

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (3)..(3)
<223> OTHER INFORMATION: a, c, t or g
<220> FEATURE:
<221> NAME/KEY: modified_base
<222> LOCATION: (6)..(6)
<223> OTHER INFORMATION: a, c, t or g
<220> FEATURE:

<221> NAME/KEY: modified_base
<222> LOCATION: (15)..(15)
<223> OTHER INFORMATION: a, c, t or g

<400> SEQUENCE: 6 gcnacnagya ayccngc 17

<210> SEQ ID NO 7
<211> LENGTH: 17
<212> TYPE: RNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (9)..(9)
<223> OTHER INFORMATION: a, c, u or g

<400> SEQUENCE: 7 uacguyagnc uyuadau 17

<210> SEQ ID NO 8
<211> LENGTH: 17
<212> TYPE: RNA
<213> ORGANISM: Artificial Sequence
<220> FEATURE:
<223> OTHER INFORMATION: Description of Artificial Sequence: Synthetic
primer

<400> SEQUENCE: 8 uacguyucrc uyuadau 17

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
probe

<400> SEQUENCE: 9 catttgatcc taaaaatctg atgca 25

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 10 gcaaccagca atcctgca 18

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 11 taaatttcgg actgcatcag 20

<210> SEQ ID NO 12
<211> LENGTH: 53

<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: CDS
<222> LOCATION: (1)..(53)

<400> SEQUENCE: 12

```
gca acc agc aat cct gca ttt gat cct aaa aat ctg atg cag tcc gaa       48
Ala Thr Ser Asn Pro Ala Phe Asp Pro Lys Asn Leu Met Gln Ser Glu
1               5                   10                  15

att ta                                                                53
Ile Tyr
```

<210> SEQ ID NO 13
<211> LENGTH: 53
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 13

```
taaatttcgg actgcatcag atttttagga tcaaatgcag gattgctggt tgc            53
```

<210> SEQ ID NO 14
<211> LENGTH: 122
<212> TYPE: DNA
<213> ORGANISM: Proteus vulgaris

<400> SEQUENCE: 14

```
gatatcactc aatcattaaa tttaggcaca acgatgggct atcagcgtta tgacaaattt     60

aatgaaggac gcattggttt cactgttagc cagcgtttct aaggagaaaa ataatgccga    120

ta                                                                   122
```

<210> SEQ ID NO 15
<211> LENGTH: 60
<212> TYPE: DNA
<213> ORGANISM: Phaseolus vulgaris

<400> SEQUENCE: 15

```
atgacaaatt taatgaagga cgcattggtt tcactgttag ccagcgtttc taaggagaaa     60
```

<210> SEQ ID NO 16
<211> LENGTH: 400
<212> TYPE: DNA
<213> ORGANISM: Proteus vulgaris
<220> FEATURE:
<221> NAME/KEY: CDS
<222> LOCATION: (296)..(400)

<400> SEQUENCE: 16

```
cagactgctt atggcaaatt aaccccctct cttaatcttc gttattcaaa gatattgcag     60

gtgacaatga tatcaatcaa cgccacagcc ttacctattt taatacaggg ggaagtacct    120

ttgatattaa aggaaatacc gttggtggtg acattattag tgcggaatta ggtgcaaatc    180

tcgatatcac tcaatcatta aatttaggca caacgatggg ctatcagcgt tatgacaaat    240

ttaatgaagg acgcattggt ttcactgtta gccagcgttt ctaaggagaa aaata atg     298
                                                             Met
                                                             1

ccg ata ttt cgt ttt act gca ctt gca atg aca ttg ggg cta tta tca      346
Pro Ile Phe Arg Phe Thr Ala Leu Ala Met Thr Leu Gly Leu Leu Ser
```

-continued

```
            5                   10                  15

gcg cct tat aac gcg atg gca gcc acc agc aat cct gca ttt gat cct      394
Ala Pro Tyr Asn Ala Met Ala Ala Thr Ser Asn Pro Ala Phe Asp Pro
        20                  25                  30

aaa aat                                                              400
Lys Asn
    35


<210> SEQ ID NO 17
<211> LENGTH: 35
<212> TYPE: PRT
<213> ORGANISM: Proteus vulgaris

<400> SEQUENCE: 17

Met Pro Ile Phe Arg Phe Thr Ala Leu Ala Met Thr Leu Gly Leu Leu
1               5                   10                  15

Ser Ala Pro Tyr Asn Ala Met Ala Ala Thr Ser Asn Pro Ala Phe Asp
            20                  25                  30

Pro Lys Asn
        35
```

What is claimed is:

[1. An isolated nucleic acid fragment encoding chondroitinase ABC, comprising the nucleotide sequence of SEQ ID NO: 1.]

[2. An expression vector comprising the nucleic acid as defined in claim 1 operably linked to a regulatory sequence.]

[3. A host cell transformed with the expression vector as defined in claim 2.]

4. A host cell of claim [3] *23* wherein the cell is eukaryotic.

5. A host cell of claim [3] *23* wherein the cell is prokaryotic.

[6. A method of producing chondroitinase ABC protein comprising: culturing the host cell as defined in claim 2 under conditions appropriate for expression; and isolating chondroitinase ABC protein from the culture.]

[7. An isolated nucleic acid encoding chondroitinase ABC comprising a nucleotide sequence which differs from the nucleotide sequence of SEQ ID NO: 1, due to degeneracy in the genetic code.]

[8. An expression vector comprising the nucleic acid as defined in claim 7 operably linked to a regulatory sequence.]

[9. A host cell transformed with the expression vector as defined in claim 8.]

[10. A method of producing chondroitinase ABC protein comprising:

culturing the host cell as in defined in claim 9 under conditions appropriate for expression; and isolating chondroitinase ABC protein from the culture.]

11. An isolated nucleic acid fragment comprising [the coding region of chondroitinase ABC and having a nucleotide sequence consisting of] nucleotides [297-3288] *73 to 3066* of SEQ ID NO: 1.

12. An expression vector comprising the nucleic acid of claim 11 operably linked to a regulatory sequence.

13. A host cell transformed with the expression vector of claim 12.

14. A method of producing chondroitinase ABC protein comprising: culturing the host cell as in defined in claim 13 under conditions appropriate for expression; and isolating chondroitinase ABC protein from the culture.

15. An isolated nucleic acid comprising a nucleotide sequence which differs from nucleotides [297-3288] *73 to 3066* of SEQ ID NO: 1, due to degeneracy in the genetic code.

16. An expression vector comprising the nucleic acid as defined in claim 15 operably linked to a regulatory sequence.

[17. An isolated nucleic acid fragment comprising nucleotides 2160-3288 of SEQ ID NO: 1.]

[18. An expression vector comprising the nucleic acid as defined in claim 17 operably linked to a regulatory sequence.]

[19. An isolated nucleic acid comprising a nucleotide sequence which differs from nucleotides 2160-3288 of SEQ ID NO: 1, due to degeneracy in the genetic code.]

[20. An expression vector comprising the nucleic acid as defined in claims operably linked to a regulatory sequence.]

21. An isolated nucleic acid fragment comprising the coding region of the nucleotide sequence of SEQ ID NO: 1.

22. An expression vector comprising the nucleic acid as defined in claim 21 operably linked to a regulatory sequence.

23. A host cell transformed with the expression vector as defined in claim 22.

24. A method of producing chondroitinase ABC protein comprising:

culturing the host cell as in defined in claim 23 under conditions appropriate for expression; and isolating chondroitinase ABC protein from the culture.

25. An isolated nucleic acid comprising a nucleotide sequence which differs from the coding region of SEQ ID NO: 1, due to degeneracy in the genetic code.

26. An expression vector comprising the nucleic acid as defined in claim 25 operably linked to a regulatory sequence.

27. A host cell transformed with the expression vector as defined in claim 26.

28. A method of producing chondroitinase ABC protein comprising: culturing the host cell as in defined in claim 27 under conditions appropriate for expression; and isolating chondroitinase ABC protein from the culture.

*29. An isolated nucleic acid fragment encoding chondroitinase ABC, wherein the nucleic acid comprises a nucleotide sequence of the insert of pCHS6 obtained from E. coli XL1-Blue/pCHS6 deposited at Accession NO. FERM BP-4170 .*

* * * * *